(12) United States Patent
Papp et al.

(10) Patent No.: US 9,585,779 B2
(45) Date of Patent: Mar. 7, 2017

(54) SEGMENTED SCAFFOLD DESIGNS

(71) Applicant: Abbott Cardiovascular Systems Inc., Santa Clara, CA (US)

(72) Inventors: John E. Papp, Temecula, CA (US); Syed Faiyaz Ahmed Hossainy, Hayward, CA (US); Michael Ngo, San Jose, CA (US); Chad Abunassar, San Francisco, CA (US); Boris Anukhin, Santa Cruz, CA (US); Mikael Trollsas, San Jose, CA (US); Lewis B. Schwartz, Lake Forest, IL (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 14/333,354

(22) Filed: Jul. 16, 2014

(65) Prior Publication Data

US 2014/0330361 A1    Nov. 6, 2014

Related U.S. Application Data

(63) Continuation of application No. 13/584,678, filed on Aug. 13, 2012, now Pat. No. 8,834,556.

(51) Int. Cl.

| | | |
|---|---|---|
| *A61F 2/06* | (2013.01) | |
| *A61F 2/90* | (2013.01) | |
| *A61F 2/89* | (2013.01) | |
| *A61F 2/915* | (2013.01) | |
| *A61F 2/958* | (2013.01) | |

(Continued)

(52) U.S. Cl.
CPC .................. *A61F 2/90* (2013.01); *A61F 2/86* (2013.01); *A61F 2/89* (2013.01); *A61F 2/915* (2013.01); *A61F 2/958* (2013.01); *A61F 2002/826* (2013.01); *A61F 2002/91591* (2013.01); *A61F 2230/0013* (2013.01); *A61F 2230/0054* (2013.01)

(58) Field of Classification Search
CPC .... A61F 2/89; A61F 2/915; A61F 2/86; A61F 2/90; A61F 2002/826; A61F 2002/91591; A61F 2230/0054; A61F 2230/0013; A61F 2220/0025
USPC ...................................................... 623/1.16
See application file for complete search history.

(56) References Cited

U.S. PATENT DOCUMENTS

| | | |
|---|---|---|
| 4,733,665 A | 3/1988 | Palmaz |
| 5,064,435 A | 11/1991 | Porter |
| 5,316,023 A | 5/1994 | Palmaz et al. |

(Continued)

FOREIGN PATENT DOCUMENTS

| | | | |
|---|---|---|---|
| WO | WO 98/20810 | 5/1998 | |
| WO | WO-00/15151 A1 * | 3/2000 | ............... A61F 2/89 |

(Continued)

OTHER PUBLICATIONS

International Search Report and Written Opinion for PCT/US2012/043497, mailed Sep. 11, 2012, 6 pgs.

(Continued)

*Primary Examiner* — Paul Prebilic
(74) *Attorney, Agent, or Firm* — Squire Patton Boggs (US) LLP

(57) ABSTRACT

Segmented scaffolds composed of disconnected scaffold segments with overlapping end rings are disclosed. Scaffolds with at least one discontinuous link are also disclosed.

4 Claims, 22 Drawing Sheets

(51) Int. Cl.
*A61F 2/86* (2013.01)
*A61F 2/82* (2013.01)

(56) References Cited

U.S. PATENT DOCUMENTS

| | | | |
|---|---|---|---|
| 5,827,321 A | 10/1998 | Roubin et al. | |
| 5,879,381 A | 3/1999 | Moriuchi et al. | |
| 6,096,072 A * | 8/2000 | Kanesaka | A61F 2/91 623/1.15 |
| 6,171,334 B1 * | 1/2001 | Cox | A61F 2/91 623/1.15 |
| 6,251,134 B1 * | 6/2001 | Alt | A61F 2/90 606/194 |
| 6,258,117 B1 | 7/2001 | Camrud et al. | |
| 6,270,524 B1 | 8/2001 | Kim | |
| 6,945,993 B2 | 9/2005 | Kveen et al. | |
| 7,175,654 B2 * | 2/2007 | Bonsignore | A61F 2/91 623/1.11 |
| 7,294,146 B2 | 11/2007 | Chew et al. | |
| 7,357,942 B2 | 4/2008 | Burke et al. | |
| 7,481,835 B1 | 1/2009 | Pacetti et al. | |
| 7,625,401 B2 | 12/2009 | Clifford et al. | |
| 8,834,556 B2 * | 9/2014 | Papp | A61F 2/89 623/1.16 |
| 2001/0044651 A1 | 11/2001 | Steinke et al. | |
| 2002/0055768 A1 | 5/2002 | Hess et al. | |
| 2002/0138131 A1 | 9/2002 | Solovay et al. | |
| 2003/0040771 A1 | 2/2003 | Hyodoh et al. | |
| 2003/0040772 A1 | 2/2003 | Hyodoh et al. | |
| 2003/0074049 A1 | 4/2003 | Hoganson et al. | |
| 2003/0199969 A1 | 10/2003 | Steinke et al. | |
| 2004/0186551 A1 | 9/2004 | Kao et al. | |
| 2004/0243217 A1 | 12/2004 | Andersen et al. | |
| 2005/0033399 A1 | 2/2005 | Richter | |
| 2005/0125051 A1 | 6/2005 | Eidenschink et al. | |
| 2005/0182477 A1 | 8/2005 | White | |
| 2005/0182479 A1 | 8/2005 | Bonsignore et al. | |
| 2006/0122691 A1 | 6/2006 | Richter | |
| 2006/0217795 A1 | 9/2006 | Besselink et al. | |
| 2006/0265048 A1 * | 11/2006 | Cheng | A61F 2/91 623/1.15 |
| 2007/0219612 A1 * | 9/2007 | Andreas | A61B 17/12022 623/1.11 |
| 2007/0219642 A1 | 9/2007 | Richter | |
| 2009/0076584 A1 | 3/2009 | Mao et al. | |
| 2009/0182413 A1 | 7/2009 | Burkart et al. | |
| 2009/0248131 A1 | 10/2009 | Greenan | |
| 2010/0042202 A1 | 2/2010 | Ramzipoor et al. | |
| 2010/0191323 A1 | 7/2010 | Cox | |
| 2010/0256728 A1 | 10/2010 | Rea Peterson | |
| 2010/0324667 A1 | 12/2010 | King | |
| 2011/0066225 A1 | 3/2011 | Trollsas et al. | |
| 2011/0190871 A1 | 8/2011 | Trollsas | |
| 2011/0190872 A1 | 8/2011 | Anukhin et al. | |
| 2011/0288622 A1 | 11/2011 | Chan et al. | |
| 2012/0065722 A1 | 3/2012 | Pacetti | |
| 2012/0303112 A1 * | 11/2012 | Armstrong | A61F 2/07 623/1.16 |
| 2013/0268045 A1 | 10/2013 | Papp et al. | |

FOREIGN PATENT DOCUMENTS

| | | | |
|---|---|---|---|
| WO | WO-01/30271 A2 * | 5/2001 | A61F 2/90 |
| WO | WO 03/022178 | 3/2003 | |
| WO | WO 03/053284 | 7/2003 | |

OTHER PUBLICATIONS

International Search Report for PCT/US2013/033141, mailed Jun. 6, 2013, 11 pgs.

* cited by examiner

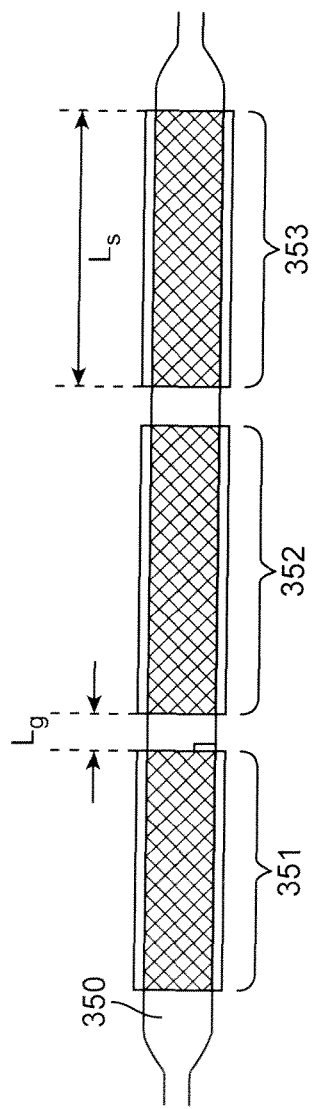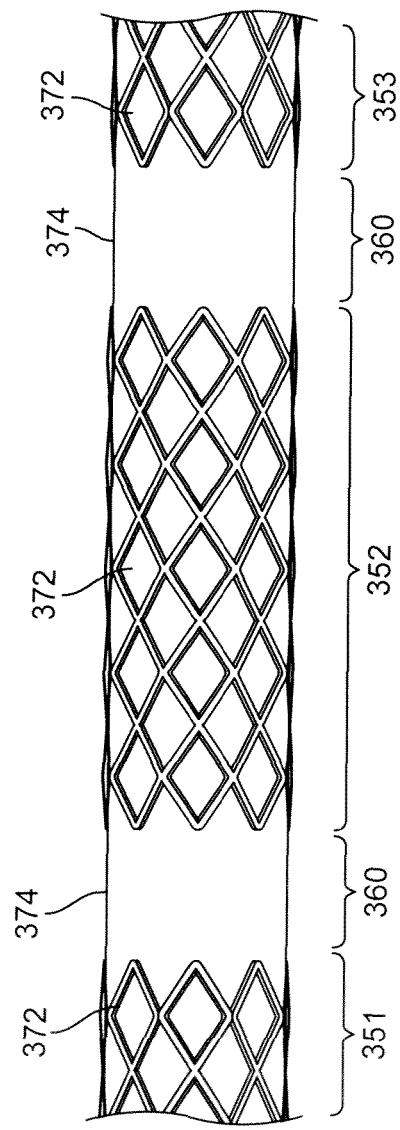
FIG. 5
FIG. 6

SEGMENTED SCAFFOLD DESIGNS

BACKGROUND OF THE INVENTION

Field of the Invention

This invention relates to methods of treatment of blood vessels with polymeric medical devices, in particular, stent scaffolds.

Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffold or scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of acute closure and restenosis as compared to balloon angioplasty.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. A medicated stent may be fabricated by coating the surface of either a metallic or polymeric scaffold with a bioresorbable polymeric carrier that includes an active or bioactive agent or drug. Polymeric scaffolding may also serve as a carrier of an active agent or drug by incorporating a drug throughout the scaffolding material.

The stent must be able to satisfy a number of mechanical requirements. The stent must have sufficient radial strength so that it is capable of withstanding the structural loads, namely radial compressive forces, imposed on the stent as it supports the walls of a vessel. This structural load will change as a function of time as the vessel heals, undergoes positive remodeling, or adapts to the presence of the stent. Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture.

Stents implanted in coronary arteries are primarily subjected to radial loads, typically cyclic in nature, which are due to the periodic contraction and expansion of vessels as blood is pumped to and from a beating heart. Stents implanted in peripheral blood vessels, or blood vessels outside the coronary arteries, e.g., iliac, femoral, popliteal, renal and subclavian arteries, however, can undergo significant nonpulsatile forces and must be capable of sustaining both radial forces and crushing or pinching loads. These stent types are implanted in vessels that are closer to the surface of the body, and may be close to joints. Because these stents are close to the surface of the body, they are particularly vulnerable to crushing or pinching loads, which can partially or completely collapse the stent and thereby block fluid flow in the vessel.

The superficial femoral artery (SFA), in particular, can subject a scaffold to various nonpulsatile forces, such as radial compression, torsion, flexion, and axial extension and compression, which place a high demand on the mechanical performance of implants.

Thus, in addition to high radial strength, stents or scaffolds for peripheral vessels such as the SFA, require a high degree of crush recovery. The term "crush recovery" is used to describe how the scaffold recovers from a pinch or crush load, while the term "crush resistance" is used to describe the minimum force required to resist a permanent deformation of a scaffold.

Stents made from biostable or non-bioerodible materials, such as metals, have become the standard of care for percutaneous coronary intervention (PCI) as well as in peripheral applications, such as the superficial femoral artery (SFA), since such stents have been shown to be capable of preventing early and late recoil and restenosis. In the SFA, where the artery undergoes extensive movement, self expanding stents made from materials such as Nitinol are the standard of care.

However, in many treatment applications, the presence of a stent in a body is necessary for a limited period of time until its intended function of, for example, maintaining vascular patency and/or drug delivery is accomplished. Moreover, it is believed that biodegradable scaffolds allow for improved healing of the anatomical lumen since they allow the vessel to return to its natural state as compared to metal stents, which may lead to a reduced incidence of late stage thrombosis. In these cases, there is a desire to treat a vessel using a polymer scaffold, in particular a bioerodible polymer scaffold, as opposed to a metal stent, so that the prosthesis's presence in the vessel is for a limited duration.

There are numerous challenges to overcome when developing a polymer scaffold, particularly in peripheral blood vessels, or blood vessels outside the coronary arteries in which a stent is subjected to both radial forces and nonpulsatile forces. One way of addressing the adverse effects of nonpulsatile forces is to implant stents as a series of disconnected segments. In this way, the transmission of nonpulsatile forces along the stent are reduced or eliminated.

SUMMARY OF THE INVENTION

Embodiments of the present invention include a segmented scaffold comprising: two or more radially expandable disconnected scaffold segments arranged end to end, wherein each segment includes two or more undulating cylindrical rings composed of struts, and wherein rings at an end of each segment comprise peak undulations projecting longitudinally outward from the end of the segment and comprise valley undulations extending longitudinally toward the segment, and wherein the peak and valley undulations of adjacent rings overlap.

Embodiments of the present invention include a method of delivering a scaffold: providing a segmented scaffold crimped over a delivery balloon, the segmented scaffold comprising two or more radially expandable disconnected scaffold segments arranged end to end, wherein each end of the segments comprises undulating cylindrical rings composed of struts and wherein undulations of adjacent segments overlap; and expanding the scaffold segments to a deployment diameter, wherein the undulations of the adjacent segments overlap at the deployed diameter.

Embodiments of the present invention include a radially expandable scaffold segment comprising: two or more connected undulating cylindrical rings composed of struts, wherein the undulating rings of each segment form a plurality of diamond-shaped cells with two pairs of opposing vertices, one pair being longitudinally aligned and one pair being circumferentially aligned, and wherein alternating diamonds around at least one end ring are omitted to form peak and valley undulations along the at least one end ring with a longitudinal length that is a longitudinal length of the diamond-shaped cells.

Embodiments of the present invention include a scaffold comprising: a plurality of scaffold segments in a crimped reduced configuration; and at least one discontinuous linking element between adjacent segments comprising a discontinuity located between the adjacent segments.

Embodiments of the present invention include a method of modifying a scaffold comprising: providing a scaffold in a crimped reduced configuration, wherein the scaffold comprises longitudinal scaffold segments and linking elements connecting adjacent scaffold segments; and creating a discontinuity in at least one linking element between at least one set of adjacent segments.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

FIG. 5 depicts scaffold segments of a segmented scaffold mounted over a balloon in a folded configuration.

FIG. 6 is a schematic illustration of a segmented scaffold with segments illustrating the reduced diameter of unsupported sections of the vessel wall between the segments.

DETAILED DESCRIPTION OF THE INVENTION

Coronary arteries refer generally to arteries that branch off the aorta to supply the heart muscle with oxygenated blood. Peripheral arteries refer generally to blood vessels outside the heart. In both coronary artery disease and peripheral artery disease, the arteries become hardened and narrowed or stenotic and restrict blood flow. In the case of the coronary arteries, blood flow is restricted to the heart, while in the peripheral arteries blood flow is restricted leading to the kidneys, stomach, arms, legs, feet, and brain. The narrowing is caused by the buildup of cholesterol and other material, called plaque, on the inner walls of the vessel. Such narrowed or stenotic portions are often referred to as lesions. Arterial disease also includes the reoccurrence of stenosis or restenosis that occurs after an angioplasty treatment. Although there are probably several mechanisms that lead to restenosis of arteries, an important one is the inflammatory response, which induces tissue proliferation around an angioplasty site. The inflammatory response can be caused by the balloon expansion used to open the vessel, or if a stent is placed, by the foreign material of the stent itself.

A stent, a stent scaffold, or scaffold includes a plurality of cylindrical rings connected or coupled with linking elements. When deployed in a section of a vessel, the cylindrical rings are load bearing and support the vessel wall at an expanded diameter or a diameter range due to cyclical forces in the vessel. Load bearing refers to the supporting of the load imposed by radial inwardly directed forces. Structural elements, such as the linking elements or struts primarily serve to maintain stability and connectivity between the rings. For example, a stent may include a scaffold composed of a pattern or network of interconnecting structural elements or struts.

Figure 1:
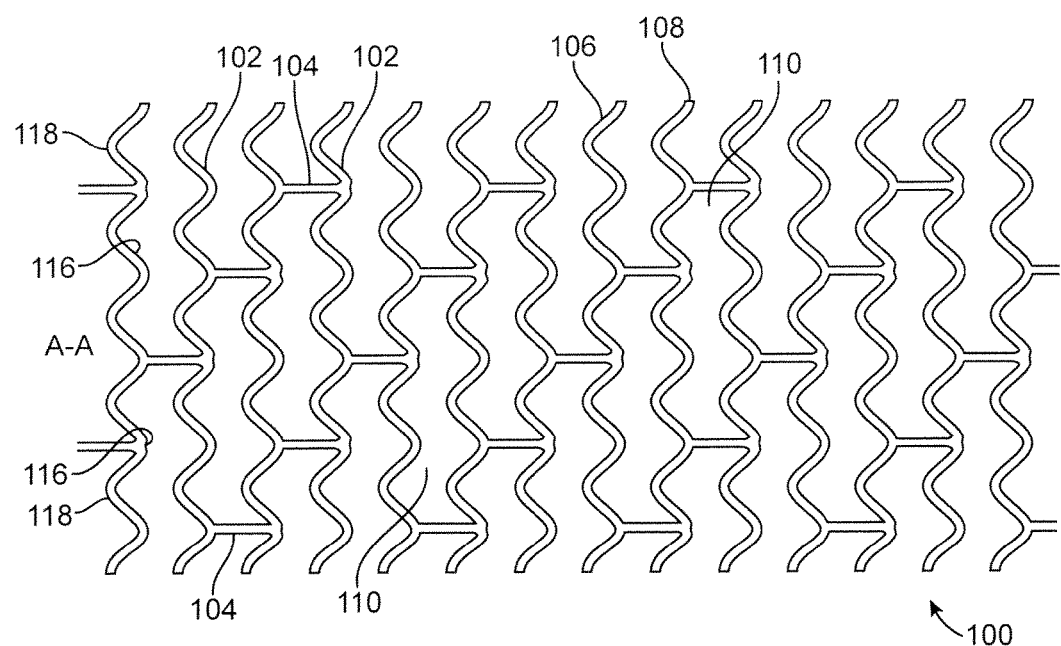
FIG. 1 depicts an exemplary stent scaffold.

FIG. 1 illustrates a portion of an exemplary prior art stent or scaffold pattern 100 shown in a flattened view. The pattern 100 of FIG. 1 represents a tubular scaffold structure so that an axis A-A is parallel to the central or longitudinal axis of the scaffold. FIG. 1 shows the scaffold in a state prior to crimping or after deployment. Pattern 100 is composed of a plurality of ring struts 102 and link struts 104. The ring struts 102 form a plurality of cylindrical rings, for example, rings 106 and 108, arranged about the cylindrical axis A-A. The rings have an undulating or sinusoidal structure with alternating crests or peaks 116 and troughs or valleys 118. The rings are connected by the link struts 104. The scaffold has an open framework of struts and links that define a generally tubular body with gaps 110 in the body defined by rings and struts. A cylindrical tube may be formed into this open framework of struts and links by a laser cutting device that cuts such a pattern into a thin-walled tube that may initially have no gaps in the tube wall.

The structural pattern in FIG. 1 is merely exemplary and serves to illustrate the basic structure and features of a stent or scaffold pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching. The stent can then be crimped onto a balloon or catheter for delivery into a bodily lumen.

The width and/or radial thickness of the struts in a scaffold may be 80 to 400 microns, or more narrowly, 100 to 250 microns, 140 to 180 microns, 200 to 400 microns, 140 to 160 microns, or 300 to 350 microns. The thickness and width can be different. For example, the width can be at or about 350 microns (e.g., ±10 microns) and the thickness can be at or about 300 microns (e.g., ±10 microns).

Semicrystalline polymers such as poly(L-lactide) (PLLA) with glass transition temperature (Tg) above human body temperature may be suitable as materials for a totally bioresorbable scaffold since they are relatively stiff and strong at the conditions of the human body. However, they tend to be brittle at these conditions. These polymer systems exhibit a brittle fracture mechanism in which there is little plastic deformation prior to failure. As a result, a stent fabricated from such polymers can be vulnerable to fracture during fabrication and use of a scaffold, i.e., crimping, delivery, deployment, and during a desired treatment period post-implantation.

Embodiments of the present invention are applicable to endovascular treatment of coronary and peripheral disease in coronary arteries and various peripheral vessels including the superficial femoral artery, the iliac artery, and carotid artery. The embodiments are further applicable to various stent types, such as self-expandable and balloon expandable stents. The embodiments are further applicable to various stent designs including scaffolding structures formed from tubes, wire structures, and woven mesh structures. Embodiments also applicable to different materials that are permanent implants such as polymers and metals like Nitinol, Algeloy, stainless steel and cobolt chrome.

In general, the initial clinical need for a bioresorbable scaffold is to provide mechanical/structural support to maintain patency or keep a vessel open at or near the deployment diameter. The scaffold is designed to have sufficient radial strength or vessel wall support for a period of time. The vessel wall support provided by the stent allows the stented segment of the vessel to undergo healing and remodeling at the increased diameter. Remodeling refers generally to structural changes in the vessel wall that enhance its load-bearing ability.

A period of vessel wall support is required in order to obtain permanent positive remodeling and vessel healing and hence maintenance of vessel patency. As the polymer of the stent degrades, the radial strength of the scaffold decreases and the load of the vessel is gradually transferred from the scaffold to the remodeled vessel wall. In addition to the decline in radial strength, the degradation of the scaffold also causes a gradual decline in the mechanical integrity, i.e., connectivity of struts and the size and shape of the overall scaffold structure. The struts gradually resorb and disappear from the vessel.

The amount of movement experienced by a peripheral scaffold in the peripheral artery is greater than what a coronary scaffold experiences in the coronary artery. A peripheral scaffold can be subjected to a high degree of flexing, axial elongation/compression, pinching, bending, and torsion after implantation. Axial stresses on the scaffold can arise from the axial compression and extension, flexural stresses are imposed by lateral flexing, crushing forces are imparted by pinching, while helical stress can arise from torsional forces.

Such stresses are propagated along the length of the scaffold and can impart significant forces throughout the scaffold structure. The forces can cause failure in ring struts, resulting in a decrease or loss in vessel wall support provided by the scaffold. Such forces can be transmitted along the length of the scaffold by link struts that connect rings.

Link strut breakage is not inherently deleterious to either performance or safety. Bench testing and animal study results suggest that scaffold properties of radial strength, crush recovery, and crush resistance are primarily attributable to the mechanical/structural integrity of the rings in the scaffold and not the links.

Strut breakage can lead to release of fragments in the blood and tissue irritation from broken strut fragments. Fragment release could result in thrombosis. Broken fragments can be mechanically injurious to the vessel leading to tissue irritation or even vessel dissection and perforation.

Figure 2:
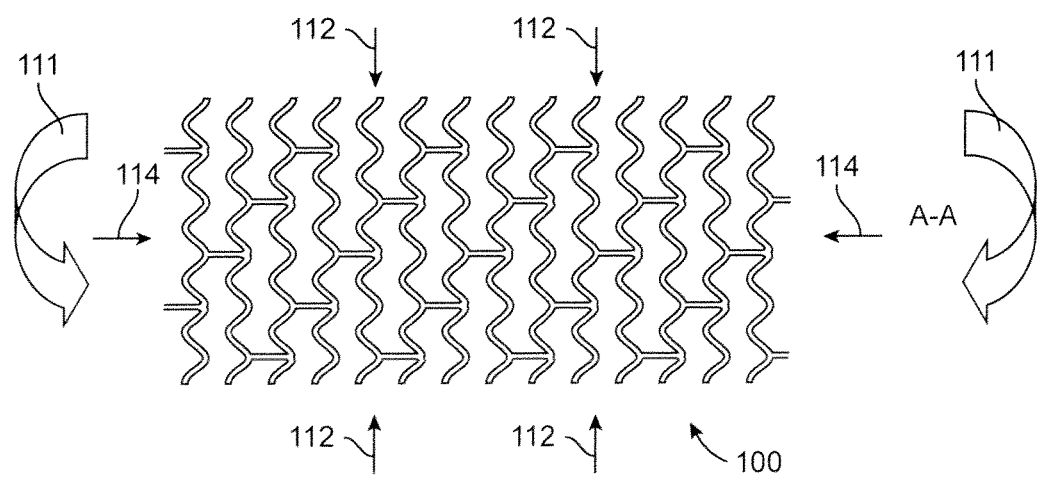
FIG. 2 depicts an exemplary scaffold pattern which shows schematically the forces acting on the scaffold.

FIG. 2 depicts the exemplary scaffold pattern 100 which shows schematically the forces acting on the peripheral scaffold. Line A-A represents the cylindrical axis of the stent. The arrows around the edges represent the forces acting on the scaffold during delivery and after deployment. Arrows 111 represent bending, arrows 112 represent radial compression, and arrows 114 represent axial compression. Bending occurs during delivery through torturous anatomy and after deployment.

Radially compressive forces on the scaffold are caused by the push back of the vessel walls on the scaffold. Axial compressive forces in the SFA arise due to movement of a leg such as during walking or bending of the leg. In the SFA, the axial compressive forces can be considerable as the vessel is compressed up to 7% or more and relaxed repeatedly up to one million cycles/year.

Cracks in the scaffold occur when it is subjected to a sufficiently high force such as resulting from bending during delivery or repetitive forces after deployment that cause fatigue. These cracks can cause a loss of radial strength or separation of struts of the scaffold that drift downstream of the scaffold.

A crack in the ring strut may cause a reduction or loss of radial strength, while a crack in the link is less damaging to the scaffold in terms of radial strength, crush resistance, and crush recovery. It is believed that if the axial forces on the scaffold were reduced, the occurrence of ring cracks would be significantly reduced. When axial forces that travel through the links to the ring struts are reduced, then the potential for ring strut fractures are also reduced.

The various embodiments of the present invention are directed to peripheral scaffolds that are subjected to significant nonpulsatile forces upon implantation. Embodiments are further directed to methods and systems for delivering such peripheral scaffolds. The embodiments of the scaffold designs are directed to reducing or eliminating strut fracture and breakage during use of the scaffold.

The embodiments are also directed to implanting such scaffolds in areas or vessels where there is no significant vessel movement such as coronary, iliac, renal etc.

The segmented scaffolds disclosed herein have advantages over non-segmented scaffods. For example, segmented scaffolds offer a substantial cost savings over conventional stent manufacturing by reducing the number of lengths of scaffolds needed in a product. In addition, the segmented scaffold segments with the disclosed diamond pattern have substantially higher radial strength (more than double that of a conventional stent) over conventional stent patterns which provides improved vessel holding open ability. This can be useful in highly calcified anatomy.

Various embodiments include a scaffold composed of axial scaffold segments that are not connected by link struts. Embodiments of such a scaffold include two or more radially expandable axial scaffold segments arranged axially end to end. The axial segments, in particular, axially adjacent segments are not connected by any physical structure or material of the scaffold. The axial segments, however, may be indirectly in contact through another structure such as a support member or a sheath. The axial segments may further be connected by structures not part of structure from which the scaffold segments are formed, such as a tube.

In general, upon deployment of the scaffold segments, forces subjected on one axial segment cannot be transmitted to other axial segments through linking struts as such forces are by linking struts of a scaffold shown in FIG. 1. The axial segments may be composed of a plurality of interconnected struts. Forces subjected to a segment can be transmitted between struts within the segment, but not between segments.

In some embodiments, the axial segments are composed of one or more cylindrical rings of struts. A cylindrical ring may be composed of undulating struts having crests and troughs. The cylindrical rings of struts that are adjacent in a segment are connected. The rings may be connected by link struts. Alternatively, the rings may be directly connected to one another without link struts. The number of rings in a segment may be one or any number greater than one. In some embodiments, a segment can have 1 or more, 2 or more, 1 to 6 rings, 1 to 3 rings, 2 to 6 rings, or 2 or 3 rings.

Upon deployment, the axial segments remain intact for a period of time and maintain a ring shape at or near the deployed diameter. Since the axial segments are not connected, they are uncoupled which prevents transmission of axial compression between segments. The decoupled axial segments retain sufficient radial strength to support the vessel at or near the deployed diameter. The decoupling of the axial segments reduces stress, for example, from axial compression that causes fracture of ring struts. The reduced ring strut fracture helps maintain the radial strength and the crush recovery and resistance to broken off struts of the scaffold floating down the vessel as emboli. The decoupling of rings reduces or prevents propagation of fracture of rings due to bending of the scaffold structure along its axis.

In some embodiments, a scaffold with disconnected axial segments can be fabricated by forming the axial segments separately. For example, a scaffold pattern can be cut into a thin-walled tube having an axial length the same as the desired axial segment. Alternatively, a scaffold can be fabricated by laser cutting a tube and then axial segments can be formed cutting the scaffold into disconnected axial segments by cutting link struts between segments or cutting the link struts between segments off entirely. Unless otherwise specified, scaffold segments or segments refer to disconnected scaffold segments or segments.

The stability of an axial segment depends on the length of the axial segment. The stability is inversely related to the length of the axial section. The susceptibility to fracture from nonpulsatile forces, however, is directly related to the length of the axial section. The length of the axial segments should be large enough so that it has a desired stability, while having reduced fracture arising from nonpulsatile forces.

The radial strength and radial stiffness of a scaffold or scaffold segment increases with the degree of connectivity of a scaffold. The degree of connectivity refers in part to the number of link struts between rings and the length of the link struts: more link struts and shorter link struts tend to increase strength and stiffness. The increase in strength and stiffness from increase in link struts has practical limitations for the FIG. 1 type designs. As the number of links is increased, the width of each ring strut is reduced to accommodate for the extra link when in the crimped state.

The stiffer the scaffold, the more susceptible the scaffold is to fracture. In the present embodiments, since compressive forces are not transmitted along an entire scaffold length, the scaffold segments can be made with a higher connectivity than a scaffold that does not have disconnected axial segments.

In the scaffolds such as the one depicted in FIG. 1, the crests of the axial rings are axially aligned or approximately axially aligned. The stiffness of the axial segments of such a scaffold can be increased by increasing the number of link struts between axially adjacent peaks of adjacent rings.

Every pair of aligned peaks between adjacent rings can be connected, every other pair of aligned peaks can be connected, or every third pair of aligned peaks can be connected by a link strut.

In some embodiments, the axial segments may be composed of rings arranged such that the crests in one ring are axially aligned or almost axially aligned with the troughs in an adjacent ring. The rings are connected by at least one link strut between an aligned crest and trough. Stiffness is greatest with a link strut between each aligned crest and trough. Greater flexibility is introduced by having fewer than every aligned crest and trough connected by a link strut. For example, only every other aligned crest and trough can be connected, or only every third aligned crest and trough can be connected by a link strut. Additionally, the length of the link struts in the axial segments can be adjusted to modify the stiffness of the axial segment. Decreasing the length of the links increases both the radial strength and radial stiffness of the axial segment since the number of rings per segment length is maximized. Alternatively, the ring crests on one ring can be aligned with the ring crests of adjacent rings. In this case, when the scaffold is crimped, the link does not occupy space between ring struts. This allows for the maximizing of ring strut width which results in higher radial strength. Such a pattern may also be described as a plurality of rings composed of diamond-shaped elements formed of struts. The elements of the rings are connected at circumferentially aligned vertices of the diamond-shaped elements. Axially adjacent rings are connected at axially aligned vertices either by a short link strut or at the intersection of vertices of elements of adjacent rings.

Figure 3A:
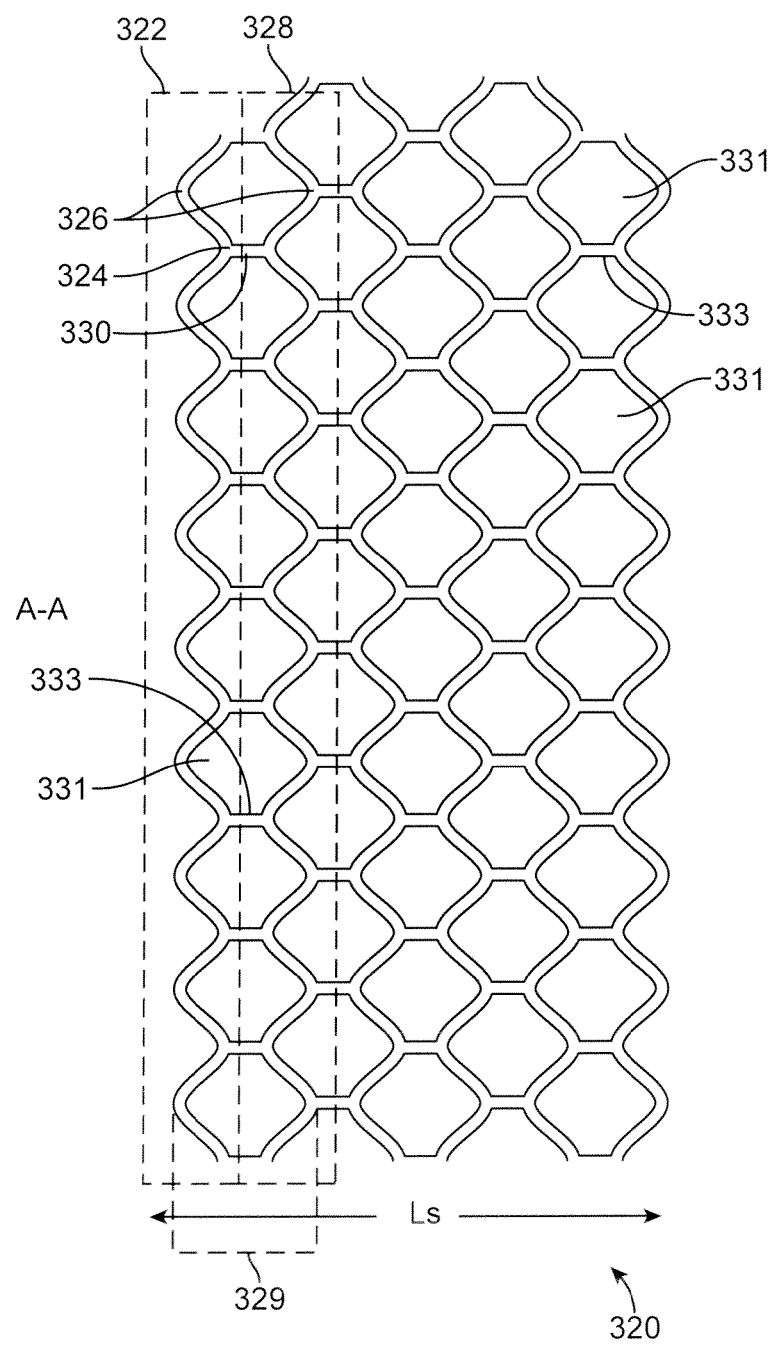
FIG. 3A depicts an exemplary scaffold segment of a segmented scaffold.

FIG. 3A depicts an exemplary axial segment 320 viewed in a flattened configuration composed of a plurality of rings of undulating struts with crests and troughs. Line A-A is the longitudinal axis of the axial segment. An exemplary ring 322 has crests 324 and troughs 326. As shown in FIG. 3A, every crest in ring 322 is connected to every trough in adjacent ring 328 by a short link strut 330. The arrangement of rings 322 and rings 328 forms a plurality of rings 329 of diamond-shaped elements 331 formed of struts. The diamond-shaped elements 331 of the rings are connected at circumferentially aligned vertices of the diamond-shaped elements.

Ls is the length of the axial segment. Ls may be 3 to 6 mm, 6 to 8 mm, 8 to 10 mm, 10 to 12 mm, or greater than 12 mm in an as cut or as fabricated configuration. Ls increases when the segment is crimped to a decreased diameter and then decreases when expanded from a crimped configuration. Length change is affected by the number of peaks in a ring and the width of the diamonds. The length change (increases or decreases) with the number of peaks and (increases or decreases) with the width of the diamonds.

Figure 3B:
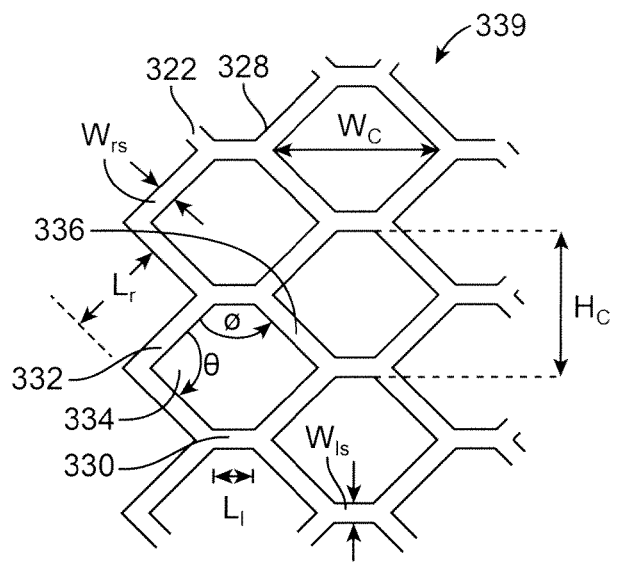
FIG. 3B depicts a close-up view of a portion of the scaffold segment in FIG. 3A illustrating various features.

FIG. 3B depicts a close-up view of a portion 339 of axial segment 320 illustrating various features. As shown in FIG. 3B, Lr is the length of a ring strut, for example, strut 332 between a crest and trough in a ring and Wrs is the width of the ring strut. $L_l$ is the length of short link strut 330 that connects crests and troughs of adjacent rings and Wls is the width of the link strut. θ is the angle at the longitudinal vertex of the diamond shaped cells, i.e., between struts 332 and 334 in a ring that intersects at a crest or trough. φ is the angle between struts 332 and 336 which are joined by short link strut 330 and a diamond-shaped cell. Hc is the height of the diamond-shaped cell and Wc is the length of the diamond-shaped cell.

θ may be 90 degrees, 90 to 95 degrees, 95 to 100 degrees, 100 to 110 degrees, or greater than 110 degrees. θ may be 90 degrees, 85 to 90 degrees, 80 to 85 degrees, 70 to 80 degrees, or less than 70 degrees. φ may be 90 degrees, 85 to 90 degrees, 80 to 85 degrees, 70 to 80 degrees, or less than 70 degrees. φ may be 90 degrees, 90 to 95 degrees, 95 to 100 degrees, 100 to 110 degrees, or greater than 110 degrees.

Exemplary values for θ and φ are about 70 and 110 degrees, respectively. Values in this range tend to reduce segment shortening from crimping to deployment. Other exemplary values for θ and φ are about 110 and 70 degrees, respectively. Values in this range tend to increase segment's radial strength and crush resistance. Another variable that affects the angles above is the lased tube diameter and the final deployed diameter. Generally, for polymers, the lased tube diameter is slightly larger than the final deployed diameter.

The segments can include radiopaque marker embedded within holes in the scaffold segment to aid in visualization of the implanted scaffold. In some embodiments, the markers are embedded in holes in the short link struts 330 of FIG. 3A. In other embodiments, the markers are embedded in holes in ring struts 332 of FIG. 3B.

When a scaffold segment is crimped, the Ls increases which is caused by bending at the vertices of the diamond-shaped elements. Specifically, when the scaffold segment is crimped, θ decreases and φ increases. When a scaffold segment is deployed, the Ls shortens which is caused by bending at the vertices of the diamond-shaped elements corresponding to an increase in θ and a decrease in φ.

The segment properties of radial strength and stiffness can be modified through adjustment of the as-cut geometrical parameters of the diamond-shaped elements. For example, radial strength and stiffness is increased by increasing Hc which results in a decrease in Wc and also corresponds to a decrease in φ and an increase in θ.

In some segment design embodiments, the diamond-shaped elements are square-shape or approximately square-shaped in the as-cut condition. In such embodiments, φ is the same or approximately the same as θ. For example, ABS (φ−θ) may be 2 or about 2 degrees or less than 2 degrees.

In other segment design embodiments, the diamond-shaped elements can be taller or greater in the circumferential direction or, Hc>Wc and φ>θ. In such embodiments, the θ−φ may be greater than 2 degrees, 2 to 4 degrees, 4 to 8 degrees, greater than 8, about 3 degrees, about 4 degrees, or about 5 degrees.

$L_l$ may be less than 10% or 10% to 20%, 20% to 30%, 30 to 40%, or greater than 40% of a ring strut length between a crest and a trough. Exemplary link struts may have a length of less than 0.01 in, 0.01 to 0.02 in, 0.02 to 0.04 in, 0.04 to 0.06 in, or greater than 0.06 in. In some embodiments, adjacent rings are connected at an intersection of the opposing crests and troughs such that a length of the link strut is effectively the width of the intersection and $L_l$ is zero.

Figure 4:
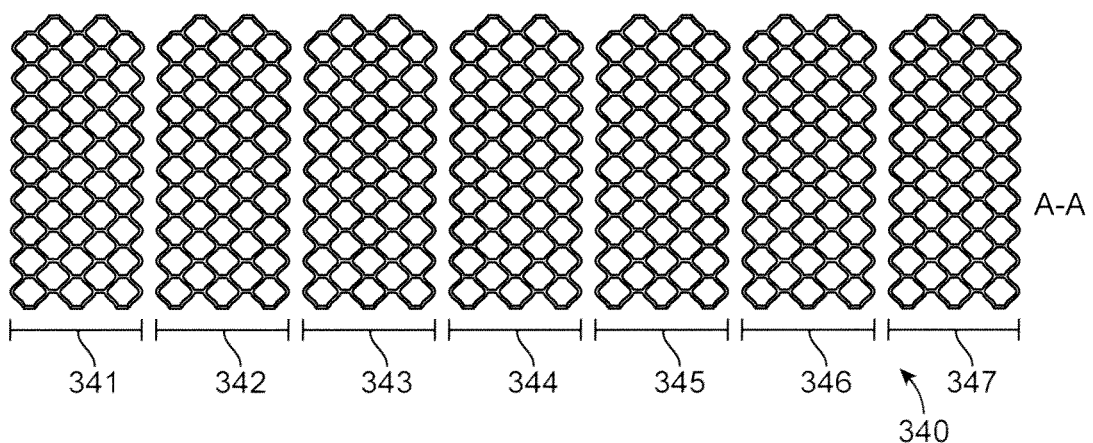
FIG. 4 depicts a segmented scaffold composed of a plurality of axial segments from FIG. 3A.

FIG. 4 depicts a segmented scaffold 340 composed of a plurality of axial segments 341 to 347, from FIG. 3A. The delivery of a scaffold composed of decoupled or disconnected axial segments can be achieved by disposing the axial segments over a catheter delivery balloon. The axial segments can be arranged end to end and spaced apart on a single balloon or multiple balloons arrange end to end. The axial segments may be crimped over the balloon to a reduced diameter configuration to allow for delivery of a vascular system to a treatment site.

Generally, stent crimping is the act of affixing a radially expandable scaffold or stent to a delivery catheter or delivery balloon so that it remains affixed to the catheter or delivery balloon until the physician desires to deliver the stent at the treatment site. Delivery balloons may be compliant, semi-compliant, or noncompliant and are made from PEBAX, nylon, or other type of common balloon material. Examples of such crimping technology which are known by one of ordinary skill in the art include a roll crimper; a collet crimper; and an iris or sliding-wedge crimper. In the sliding wedge or iris crimper, for example, adjacent pie-piece-shaped sections move inward and twist toward a scaffold in a cavity formed by the sections, much like the leaves in a camera aperture.

FIG. 5 depicts a projection of axial segments 351, 352, and 353 disposed over a balloon 350 in a deflated configuration. Axial segments are crimped tightly over the balloon in a reduced diameter configuration. A crimped configuration generally may correspond to the inner surface of the segments in contact with the outer surface of a balloon. The axial segments are spaced apart by a distance, size, or width Lg, which is the gap between segments. Lg can change during inflation and deployment of the segments to a deployed diameter due to movement of the segments and axial contraction or shortening of the segments. Lg at deployment should be large enough to avoid interference or contact of the segment ends during bodily movements. Lg at deployment should be large enough so that there is axial stability and the support of the vessel is continuous. In exemplary embodiments, the segments when deployed are spaced apart by 0.5 to 2 mm, or more narrowly, 0.5 to 1 mm, 1 to 2 mm, 2 to 3 mm. The required Lg is determined by the anatomy that the segmented scaffold will be deployed in to, i.e., in the SFA it will need to be greater than for the Iliac where vessel compression and bending are virtually zero. In general, Lg is higher for anatomies with higher vessel compression and bending.

Factors that influence a desired Lg at deployment include the axial compression in the vessel, bending of the vessel, and stability in presence of side branches coming off of a segment of the vessel where the scaffold is implanted.

When compressive loads are placed on the scaffold the axial compression may occur predominantly between segments. Generally, it is important to allow for the decrease in the spacing of the segments during compression and loading. Therefore, Lg at deployment should be large enough so that the segments do not contact or interfere with each other during axial compression. The Lg at deployment can be selected to allow for an axial compression of zero, below 7%, or 7 to 15%, or for example, about 13%.

The bending of a vessel with implanted segments results in a decrease in the Lg at the concave or inner side of the bend with the gap widening toward the convex or outer side of the bend. The segments at the inner side of the bend can interfere or make contact with each other if the initial gap is not wide enough. The Lg at deployment can be selected to allow for bending of 20 to 30 degrees or less than 30 degrees, or about 30 degrees. In this case, a 3 mm gap reduces to 0.8 mm at the inner side of the gap.

The scaffold segments may be deployed in a vessel that includes a side branch and a gap between segments that overlap this side branch. In this case, Lg can be the width of the side branch or greater or less than the width of the side branch. To maintain axial stability of a segment of a segmented scaffold over a side branch, the length of a segment needs to be longer that the side branch so that the radially supported length of the segment is typically 1.5 times the segment diameter when deployed. This diameter:length ratio can be less than a 1:1 ratio, a 1:1 ratio, a 1:1.5 ratio or a 1:2 ratio or greater. The ratio is dependent among other things on the size of the nonpulsatile forces at the delivery site. For example, the Lg at deployment can be less than 2 or 3 mm.

The diamond pattern disclosed herein tends to maximize the relative friction between the vessel wall and the segments. With this and the high radial and axial rigidity of the diamond pattern, endothelialization of the segments may be sped up and vessel irritation may be reduced. With quick endothelialization, the scaffold/vessel wall becomes a composite structure which in itself enhances the radial strength and hence crush resistance of the vessel/scaffold composite. With most, if not all of the movement transferred to the gaps between the segments, the design utilizes the natural flexibility of the vessel walls to handle any compression, bending and torsional movements.

In some embodiments, a single high radial strength and stiff scaffold segment, such as described above, may be implanted at an implant site. Implanting a single segment without additional segments may be useful in treatments involving vessels that do not undergo axial compression, torsion, or bending. Examples include the Iliac and Renal artery.

During deployment at a lesion site of a conventional balloon expandable stent or scaffold, the balloons generally start to expand at the proximal and distal ends first, producing a dog bone shape. As pressure is increased, the balloon expands in the center, expanding the scaffold in the center also.

With the segmented scaffold which can include several short scaffolds on a single balloon, the balloon can expand in a similar manner, i.e., expanding at the proximal and distal ends first, followed by expansion of a center section. Expansion at the ends first has the tendency to push the segments axially towards the center of the balloon which decreases the segment to segment gap. The gap may be decreased to the point that the segments collide with each other. This movement of the individual segments axially along the balloon during deployment, therefore, can change the segment to segment gap to an undesirably small size which can result in interference of the segments. Additionally, the segment to segment spacing will not necessarily be the same between all segments. A reduced gap or zero gap may be acceptable where nonpulsatile forces are virtually zero.

In pre-clinical animal studies, bioabsorbable polymer disconnected segmented scaffolds have been shown to have high radial strength and fracture resistance. The sections of the artery along the segments are held open at a desired diameter. However, in some cases, the sections of the artery at the gaps between the segments are not held open to the same degree as along the segments. There appears to be "sagging" or focal restenosis of the vessel wall inward into the artery lumen at the gaps between segments. For example, in a case where the gaps between the segments were on the order of 5 mm, sagging or focal restenosis was observed.

FIG. 6 is an image of bench tested segmented scaffold showing segment 352 and a portion of segments 351 and 353. The sections of vessel wall 372 along the segments are supported at a diameter of the segments. Sections 374 of the vessel wall along gaps 360 between the segments sag inward toward the lumen.

Embodiments of the present invention include segmented scaffolds and delivery thereof that reduce or prevent the vessel sagging between the segments while maintaining high radial strength and fracture resistance.

Embodiments of the present invention include deploying a segmented scaffold in a manner that the ends of the adjacent scaffolds segments overlap or are interlinked. The segments that are overlapped or interlinked are disconnected and are not in contact. The segment ends overlap. Therefore, there no gap between segments that is a strip or band with no support that completely encircles the vessel wall. Equivalently, there is no longitudinal position without support from a segment between the ends of adjacent segments that extends completely around the circumference of the vessel wall or scaffold.

Embodiments also include segmented scaffold segments in a crimped reduced state with ends of the adjacent scaffolds segments that overlap or are interlinked. The crimped scaffold segments can be crimped over a delivery balloon to allow balloon assisted delivery of the segments to a deployed state in a vessel. The scaffold segments are interlinked in a manner that upon expansion of the segments to a deployed state, the deployed segments are interlinked as described.

Although specific embodiments are described herein, the embodiments generally apply to segmented scaffold made up of segments composed of struts forming a plurality of circumferential undulating rings, the undulations include peaks and valleys, as exemplified above. Undulating can refer to, but is not limited to, to a wave-like appearance or form. The wave-like appearance can be smooth, such as sinusoidal from, or jagged, such as a zigzag form. The ends of the segments, therefore, include an undulating ring also with peaks and valleys. A peak or valley undulation refers generally to the portion of an undulation or wave on either side of a peak or valley. The peak undulations project longitudinally outward or away from the end of the segment and the valley undulations extend longitudinally inward or toward the segment.

The interlinking of two adjacent scaffold segments with the above general structure is described with respect to the peak undulation and valley undulation of neighboring end rings of adjacent segments. The peak undulations of a first ring overlap or extend into the valley undulation of an adjacent ring. Likewise, the peak undulations of the adjacent ring overlap or extend into the valleys of the first ring. The degree of overlap or interlinking can be described in terms degree of extension of the peak undulations into the valley undulations.

The peak and valley undulations in the crimped state are compressed close to one another relative to the expanded or deployed state. The segments described are provided in the crimped state with the interlinking of the neighboring rings of adjacent segments. The degree of overlap may be greater in the crimped state than the deployed state since the degree of overlap may decrease as the segments are expanded.

Figure 7:
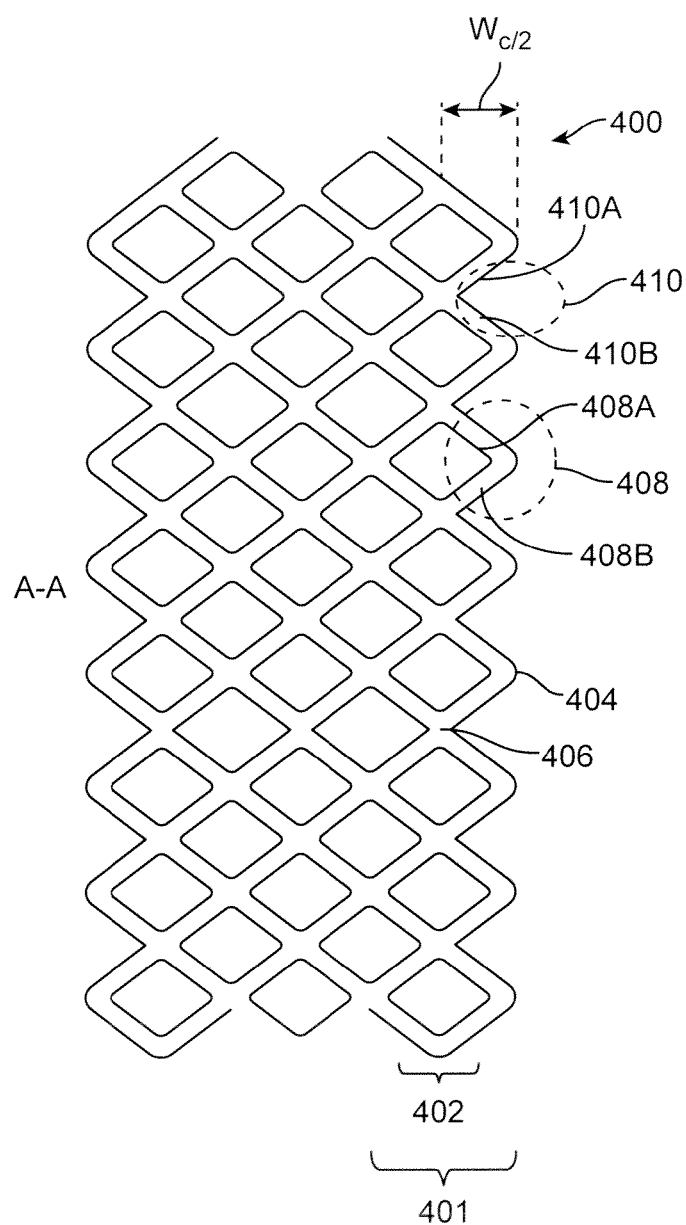
FIG. 7 depicts a flattened view of an exemplary scaffold segment 400 similar to the segment depicted in FIG. 3A.

Interlinked segmented scaffolds can be formed using the scaffolds segments described, for example, in FIGS. 3A-B and 4. FIG. 7 depicts a flattened view of another exemplary scaffold segment 400, like segment 320 depicted in FIG. 3A. Line A-A represents the longitudinal axis of the segment. Segment 400 has an end ring 401 of diamond cells made up of two undulating rings connected at peaks, one of which is undulating end ring 402 composed of peaks 404 and valleys 406. Peak undulations 408 are composed of struts 408A and 408B which extend from two adjacent valleys and meet at a peak. Valley undulations 410 are composed of struts 410A and 410B which extend from two adjacent peaks and meat at a valley. Peak undulations project longitudinally outward from the segment and valley undulations extend longitudinally inward into the segment. The height or length of the valley and peak undulations is one half the longitudinal length of a diamond, Wc/2.

A segmented scaffold can be provided in a deployed state with scaffold segments such as segment 400 that are arranged with interlinking of adjacent end rings. The peak undulations 408 can overlap or interlink with the valley undulations 410.

However, for the segment 400 such a deployed configuration may be difficult or impossible to achieve in practice. Specifically, the peak undulations may not fit into the valley undulations in a desired crimped state since the angle at the valley is very small in the crimped state. Additionally, even if the peak undulation overlaps the valley in a crimped state, the degree of overlap at crimping is small compared to the length decrease of the segment from the crimped to deployed state. When the segments are deployed, from the crimped to deployed state, the degree of overlap will decrease and may disappear when the segments are deployed.

Embodiments further include segmented scaffolds with segments that are modified to have valley undulations with a greater length or height which allow overlap in the crimped state and overlap when the segments are deployed. The degree of potential overlap is higher relative to the length change of a segment from the crimped state to a deployed state. In such embodiments, the length of the potential overlap of ends of segments can be at or about the longitudinal length of cells of the pattern. Specifically with respect to the exemplary segment 400, the length of the potential overlap is at or about the longitudinal length of a diamond cell of the segment.

Embodiments include segments which are a modification of the segments as described with an end ring of diamonds and undulating end ring of struts. The modification includes omitting diamonds of the diamond end ring at one or both ends. In particular, alternating diamonds may be omitted from one or both ends of a segment. Omitting diamonds refers to removing the struts forming every other peak undulation. For example, struts 408A and 408B in FIG. 7 may be omitted.

The resulting segment has an end ring with peak and valley undulation that provides a greater potential overlap. The degree of shortening upon expansion is unchanged. Therefore, when the modified scaffold segments that are interlinked in the crimped state are expanded to the deployed state, there is significant overlap remain in the deployed state.

Figure 8:
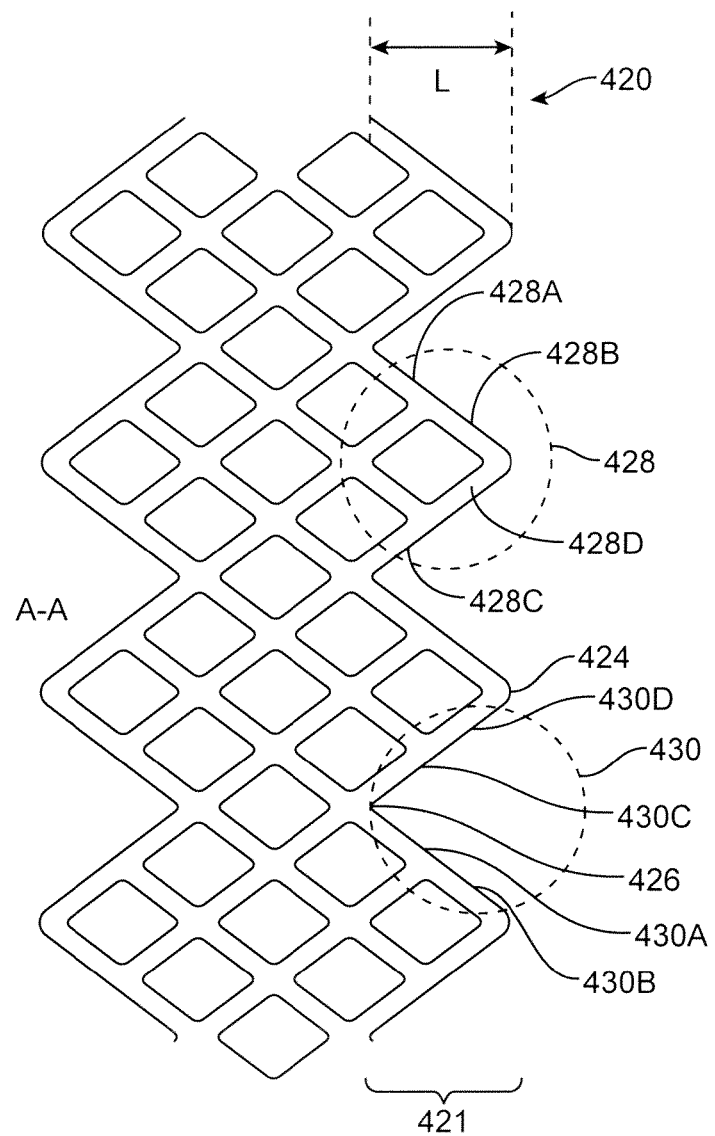
FIG. 8 depicts an exemplary segment based on the segment of FIG. 7 in which alternating diamonds are omitted one end and in-line diamonds are removed on the other end.

FIG. 8 depicts an exemplary segment 420 based on segment 400 of FIG. 7 in which alternating diamonds are omitted at each end. Equivalently, every other peak undulation is omitted on both ends of the segment. Specifically, every other pair of struts 408A and 408B are omitted. In addition, the diamonds that are omitted at opposite ends are longitudinally aligned or opposite from one another or "in-line" diamonds are omitted. Thus, the embodiment in FIG. 8 will be referred to as an "in-line segment." The modified segment, therefore, has an end ring with an undulating, zigzag structure in which the length of a "zig" and "zag" or from a valley to a peak is twice the length of a side of a diamond of a diamond cell. The longitudinal length of a peak or valley undulation is the longitudinal length of a diamond cell.

As shown in FIG. 8, segment 420 has an undulating end ring 421 composed of peaks 424 and valleys 426. Peak undulations 428 are composed of pairs of in-line struts, (428A, 428B) and (428C, 428D) which extend from two adjacent valleys and meet at a peak. Valley undulations 430 are composed of pairs of in-line struts (430A, 430B) and (430C, 430D) which extend from two adjacent peaks to a valley. Each of the two inline struts is the length of a side of the diamond cells.

Peak undulations project longitudinally outward from the segment and valley undulations extend longitudinally inward into the segment. As is shown below, the maximum potential length of overlap is one half the longitudinal length of a diamond, ½ Wc. For the in-line segment, the peaks (and valleys) of the end rings are longitudinally aligned. As shown in FIG. 8, the minimum width of segment 420 is the longitudinal length of a diamond cell, Wc.

Figure 9:
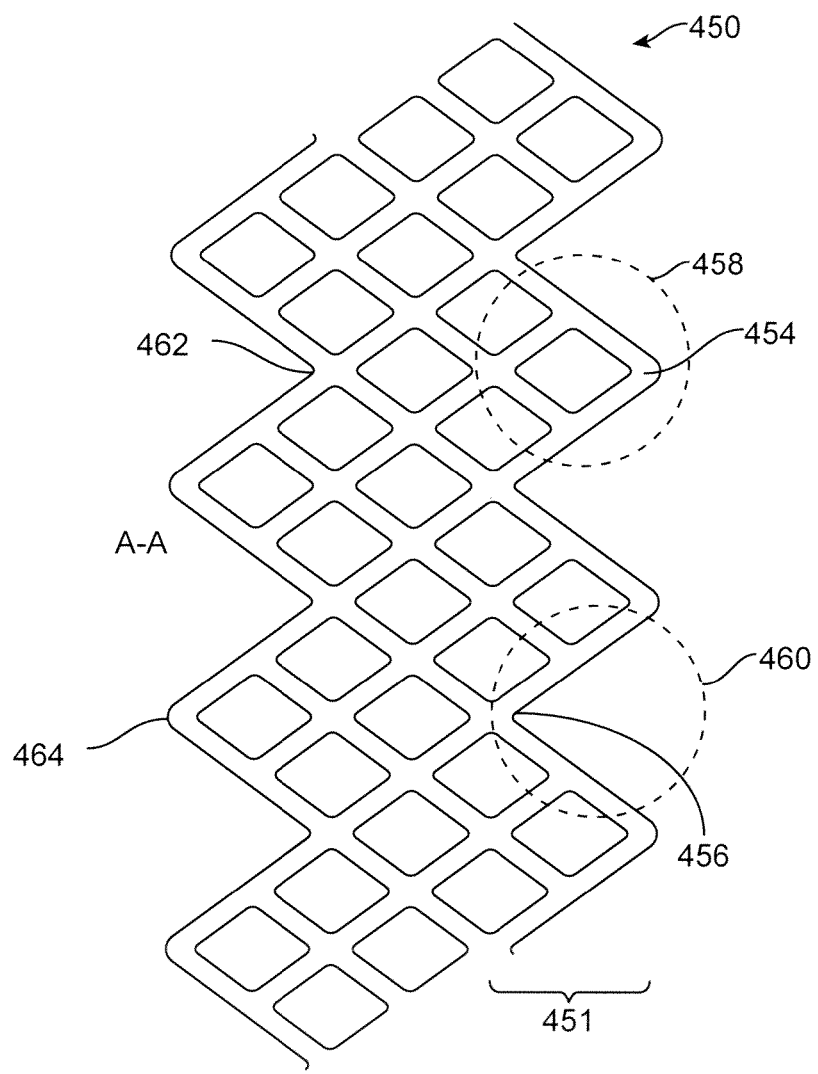
FIG. 9 depicts an exemplary segment based on the segment of FIG. 7 in which alternating diamonds are omitted one end and off-set diamonds are removed on the other end.

FIG. 9 depicts an exemplary segment 450 based on segment 400 of FIG. 7 in which alternating diamonds are omitted at both ends of the segment. Specifically, every other pair of struts 408A and 408B is omitted. Segment 450 differs from segment 420 of FIG. 8 in that omitted diamonds at one end are not longitudinally aligned with omitted diamonds at the other end. The diamonds omitted at one end are circumferentially off-set by one diamond cell. The embodiment in FIG. 9 will be referred to as an "off-set segment." An alternate embodiment is omitted diamonds every third or every fourth diamond around the circumference of the end ring.

As shown in FIG. 9, segment 450 has an undulating end ring 451 composed of peaks 454 and valleys 456. Peak undulations 458 are composed of two pairs of in-line struts, as described in FIG. 8, which extend from two adjacent valleys and meet at a peak. Valley undulations 460 are composed of pairs of inline struts, as described in FIG. 8, which extend from adjacent peaks to a valley. Peak undulations project longitudinally outward from the segment and valley undulations extend longitudinally inward into the segment. As shown below, the potential overlap is one half the longitudinal length of a diamond, ½ Wc. As shown in FIG. 9, the minimum width of segment 450 is twice the longitudinal length of a diamond cell, 2×Wc. Also, as shown in FIG. 9, the peaks at one end are longitudinally aligned with the valleys at the other end, for example, peak 454 is longitudinally aligned with valley 462.

Figure 10:
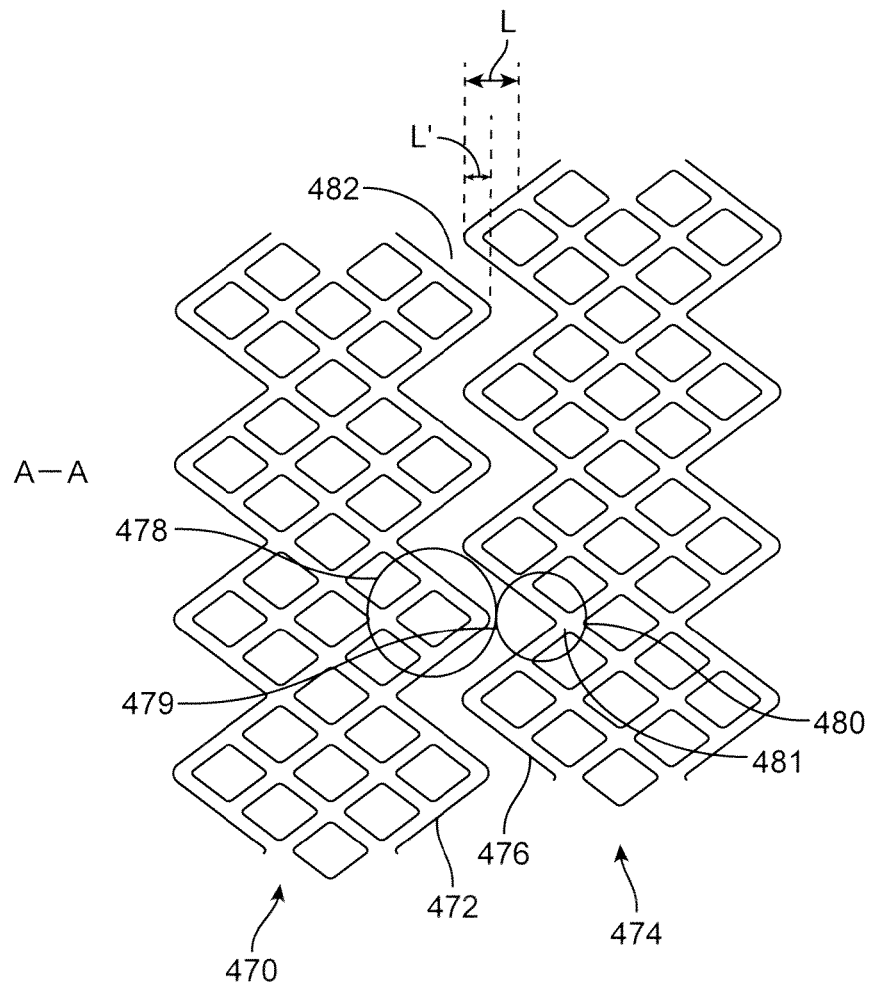
FIG. 10 depicts two in-line segments of FIG. 8 that are interlinked.

FIG. 10 depicts two in-line segments 470 and 474 which are interlinked. End ring 472 of segment 470 is interlinked with end ring 476 of segment 474. For example, peak undulation 478 of segment 470 projects into valley undulation 480 of segment 474. Each peak of the interlinking peak undulation (e.g., peak 479) is longitudinally aligned with the each valley of the interlinked valley undulation (e.g., valley 481). FIG. 10 shows the first segment 470 and second segment 474. Each of these first and second segments has undulating cylindrical rings composed of struts and forming a plurality of diamond-shaped cells. For each segment a first ring at a first end comprises alternating peak and valley undulations, a second ring at a second end comprises alternating peak and valley undulations, the peaks at the first and second ends extend in opposite directions to each other and the peaks are longitudinally aligned with the peaks of the second ring. Additionally, the first ring of the second segment is arranged with the second ring of the first segment, such that the peaks of the first ring of the second segment overlap the valleys of the second ring of the first segment.

There are various ways of defining the degree of overlap or interlinking of the segments. For example, the percent overlap of interlinking of peak undulation 478 with valley undulation 480 can be calculated from, L, the one half length of a diamond cell and the length of the overlap of the peak undulation 478 with the valley undulation 480, L′: % overlap=L′/L×100%. The degree of overlap at deployment may be 5 to 70%, or more narrowly, 5 to 20%, 20 to 30%, 30 to 40%, 40 to 50%, 50 to 60%, and 60 to 70%.

Figure 11:
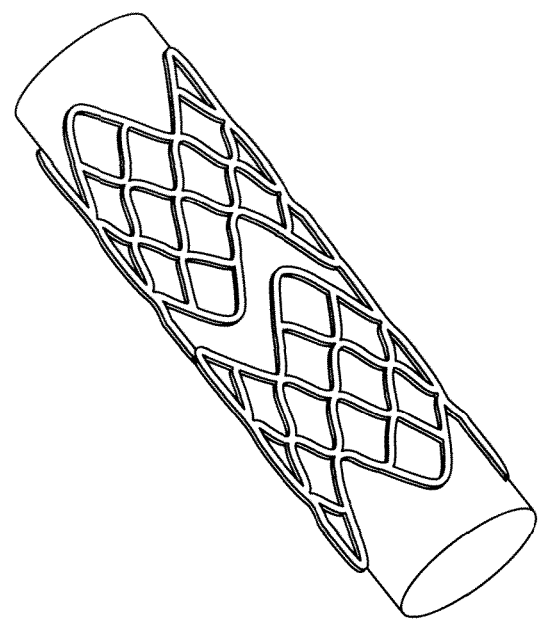
FIG. 11 depicts a three-dimensional view of two interlinked segments.

As shown in FIG. 10, there is a gap 482 between end rings 472 and 476 of segments 470 and 474, respectively. However, the gap has an undulating profile that follows the interlinking profile of end rings 472 and 476. As a result, there is no longitudinal position completely around a vessel wall that is not supported. FIG. 11 depicts a three-dimensional view of two interlinked segments.

In order for deployed segments to have overlap, the segments are provided in a crimped state with a degree of overlap. The degree of overlap is selected so that upon expansion or deployment to a target diameter, the deployed segments have a desired amount of overlap. The degree of overlap at crimping may be 50 to 100%, or more narrowly, 50 to 60%, 60 to 70%, 70 to 80%, 80 to 90%, or 90 to 100%. This overlap may be such that at the gap 482, the axial space between ring struts from a first segment to the ring struts of a second segment is the same as the ring strut spacing within the segments. This will provide a continuous uniform vessel support at the segments and across the segment gap also. In addition, gap 482 may be less than the length of a diamond, the same as the length of a diamond, or more than the length of a diamond.

Figure 12:
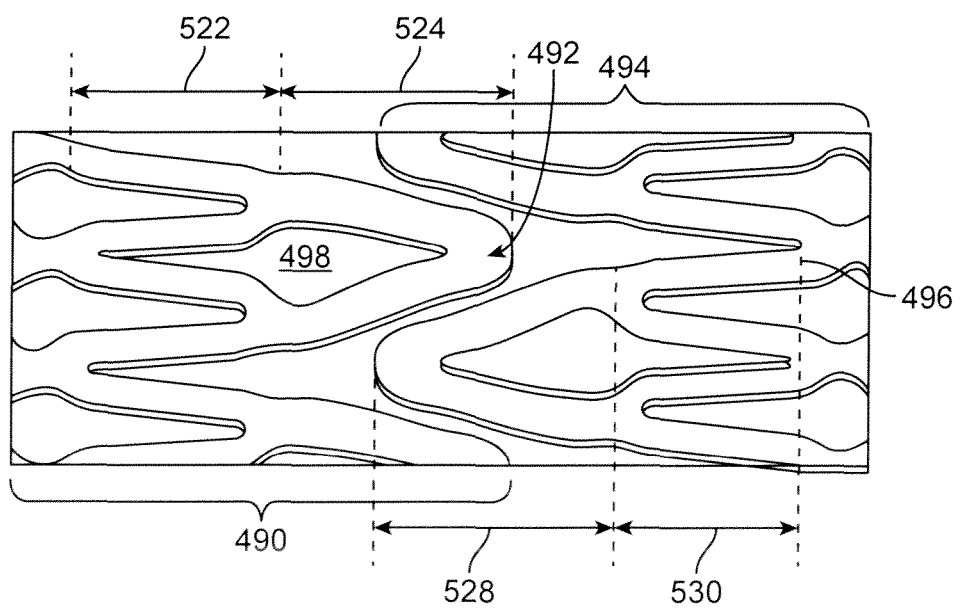
FIG. 12 depicts interlinked segments in a crimped state with about 50% ring overlap or engagement of the end rings.

FIG. 12 depicts a side view of interlinked segments 490 and 494 with omitted end ring diamonds in a crimped state with about 50% ring overlap or engagement of the end rings. For example, a peak undulation with a peak 492 is shown to be overlapping or engaged within the valley undulation with a valley 496. The opening of the diamond cell 498 is shown to have a deformed shape due to the crimped state.

Figure 13:
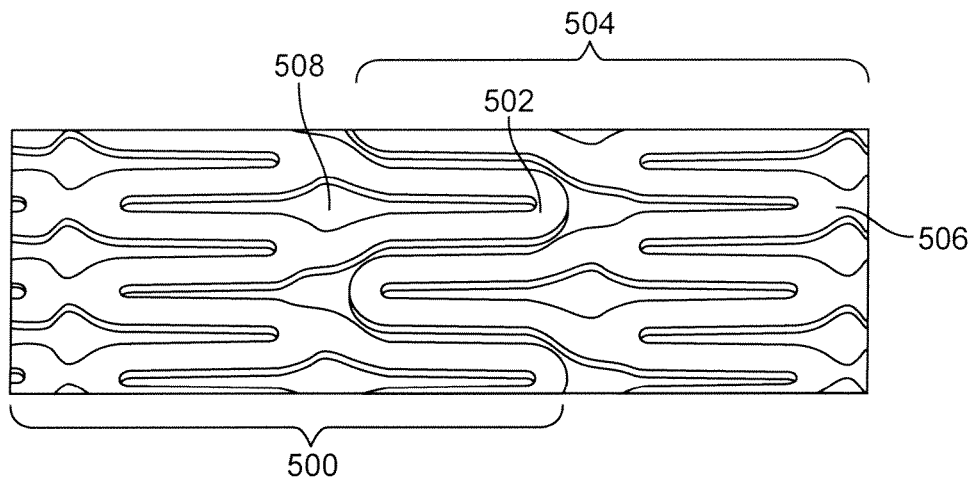
FIG. 13 depicts interlinked segments in a crimped state with about 100% ring overlap or engagement of the end rings.

FIG. 13 depicts interlinked segments 500 and 504 with omitted end ring diamonds in a crimped state with about 100% ring overlap or engagement of the end rings. For example, a peak undulation with a peak 502 is shown to be overlapping or engaged within the valley undulation with a valley 506. The opening of the diamond cell 508 is shown to be reduced significantly due to the crimped state.

Figure 14:
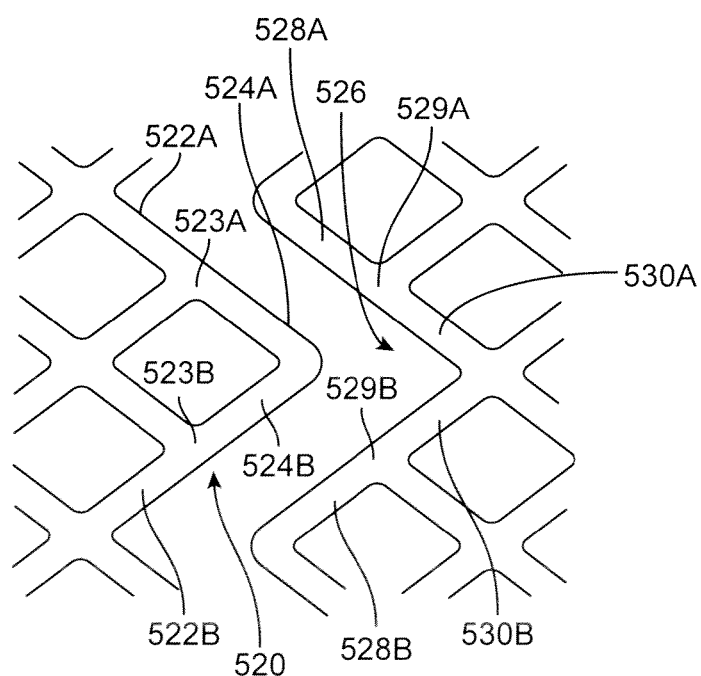
FIG. 14 depicts an expanded view of the interlinked scaffolds of FIG. 10.

The crimped interlinked segments of FIGS. 12 and 13 demonstrate how the undulations of the modified rings allow both crimping to a reduced profile and interlinking at crimped and deployed states. FIG. 14 depicts an expanded view of the interlinked scaffolds of FIG. 10. Peak undulation 520 is composed of a first portion made up of pairs of struts 524A and 524B and a second portion composed of pairs of struts 522A and 522B. Likewise, valley undulation 526 is composed of a first portion made up of pairs of struts 530A and 530B and a second portion composed of pairs of struts 528A and 528B.

When the segment is crimped, the struts that make up the peak and valley undulations bend inward. However, as shown in FIGS. 12 and 13, the first portion 524 and the second portion 522 of the peak undulation 520 bend inward to different degrees at pivot points 523A and 523B. The second portion 522 of the peak undulation bends inward to a greater degree than the first portion 524, which is within the valley undulation.

Likewise, the first portion 530 and the second portions 528 of the valley undulation 526 bend inward to different degrees at points 529A and 529B, as shown in FIGS. 12 and 13. The first portion 530 of the valley bends inward to a greater degree than the second portion 528. The closely spaced struts of the first portion cannot accommodate overlap of the peak undulation of the adjacent segment, but allows for reduction of the segments to a low profile or low diameter configuration. The struts of the second portion 528 of the valley undulation are spaced apart sufficiently to allow overlap of the first portion 524 of the peak undulation of the adjacent segment. In another embodiment, pivot points 523A and 523B may be closer together. This would result in less room needed for the interlink in the crimped state. Alternatively, the diamonds at the interlink and several rows in from the interlink could be adjusted in shape to accomplish a looser or tighter interlink fit in the crimped state. In addition the diamonds could be axially shorter, axially the same or axially longer near the end or at the end of the segments.

Figure 15:
FIG. 15 depicts an image of a deployed segmented scaffold with large segment to segment gaps.

The modified segmented scaffolds disclosed with alternating diamonds removed could be deployed in configurations that are not optimum or undesirable. These configurations may result develop during deployment from the crimped state. A non-optimum configuration includes segments with excessive segment to segment gaps in the deployed state so that the vessel is not supported adequately in the segment gaps. In such a configuration there is no overlap of the end rings or the degree of overlap of the rings is low, for example, less than 20 or 30%. FIG. 15 depicts an image of a deployed segmented scaffold with large segment to segment gaps.

Figure 16:
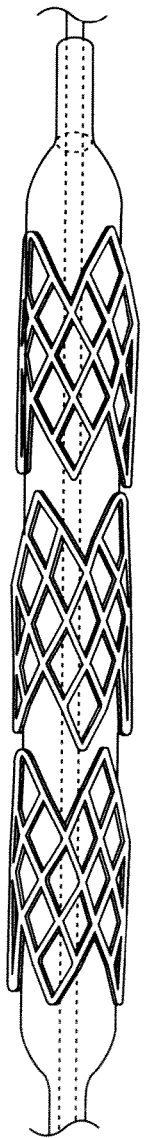
FIG. 16 depicts deployed segmented scaffolds of which the left-most segment is rotated relative to the middle segment resulting in a non-uniform gap.

In other non-optimum configurations segments may collide as the vessel is axially compressed as would happen in the Superficial Femoral Artery. Collisions can result from a configuration in which the peaks and valleys of adjacent segments are not longitudinally aligned, in contrast to segments 470 and 474 in FIG. 10. Such a configuration can result from rotation of a segment during deployment. FIG. 16 depicts deployed segmented scaffolds of which the left-most segment is rotated relative to the middle segment resulting in a non-uniform gap at "X". As a result, the segment gap is nonuniform circumferentially.

Therefore, there is a need for a way to insure that the segment gap is consistent between all segments, not excessive, and also uniform circumferentially.

Figure 17:
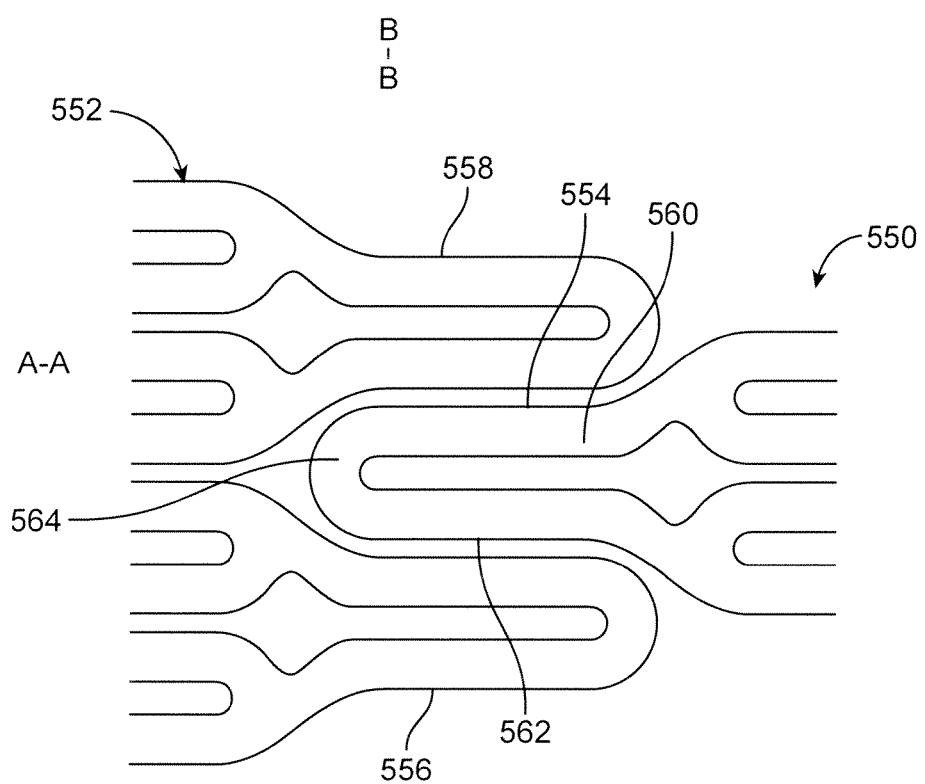
FIG. 17 depicts a schematic of part of the interlink area of the crimped segmented scaffold of FIG. 13.

FIG. 17 depicts a schematic of part of the interlink area of the crimped segmented scaffold of FIG. 13. A peak undulation 554 of segment 550 is disposed in between peak undulations 556 and 558 of segment 552 such that there is an overlap of approximately 100% between the two segments. Peak undulation 554 is made up of struts 560 and 562, the sides of a diamond cell, which extend from opposing vertices of the cell to meet at peak 564. The outer side wall surface or profile of the struts 560 and 562 is straight and smooth so that when the segments are deployed there is no interaction between the surfaces of the adjacent scaffolds that influences the relative positions of the adjacent segments.

FIGS. 18A-B and FIGS. 19-20 depict embodiments of segments that are modified to maintain a consistent segment gap which is not excessive and also reduce or prevent rotation during deployment which results in a nonuniform gap circumferentially.

Figure 18A:
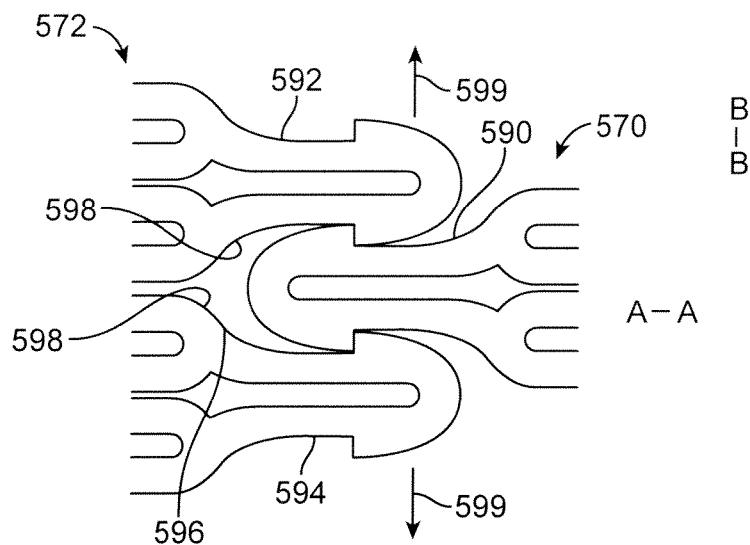
FIG. 18A depicts an interlinked region of crimped interlinked segments.
Figure 18B:
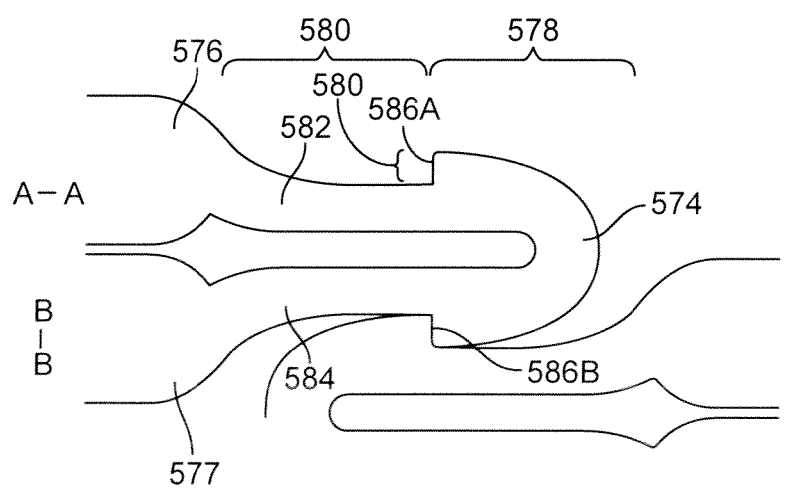
FIG. 18B depicts an expanded view of one of the peak undulations.

FIG. 18A depicts an interlinked region of crimped interlinked segments 570 and 572. FIG. 18B depicts an expanded view of one of the peak undulations. The peak undulations of the end rings of segments 570 and 572 include head portion 578 and body portion 580. Head portion 578 in the region of peak 574 has an overhang 580 on either side of peak 574 along struts 582 and 584 that extend from peak 574 to vertices 576 and 577, respectively. The overhangs 580 are situated between peak 574 and the vertices 576 and 577. The side wall surface between peak 574 and the vertices extends inward at the overhang 580 on either side of the peak undulation to form interlocking surfaces 586A and 586B.

A shown in FIG. 18A, peak undulation 590 is disposed between peak undulations 592 and 594. The overhangs of the head portion of peak undulation 590 are disposed past the overhangs of peak undulations 592 and 594 such that the interlocking surfaces of peak undulation 590 are engaged or in contact or can engage or make contact when the segments are expanded.

When crimped, the adjacent segments are mechanically held in a constant or fixed relationship to each other both circumferentially and longitudinally. The adjacent segments are held through engagement of the interlocking surfaces of the head portions of the end rings. The adjacent rings overlap longitudinally a consistent amount. Additionally, the segments are radially locked into place by the mechanical engagement of the head portions.

In addition, the crimped segments can move around tight bends in a vessel during delivery to the lesion site. Bending is accommodated at each segment to segment connection by a longitudinal space 596 between the head of each peak undulation and the side walls 598 of the end ring of the adjacent segment.

Figure 30:
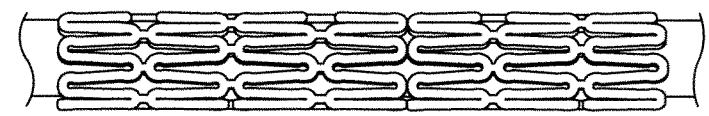
FIG. 30 depicts images of an interlinked segmented scaffold composed of two segments.
Figure 30:
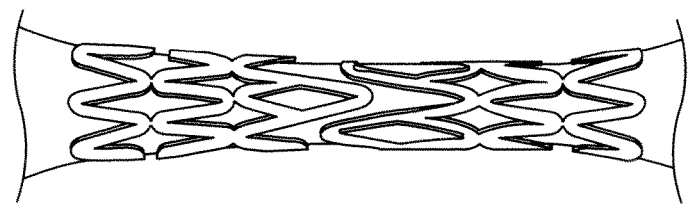
Figure 30:
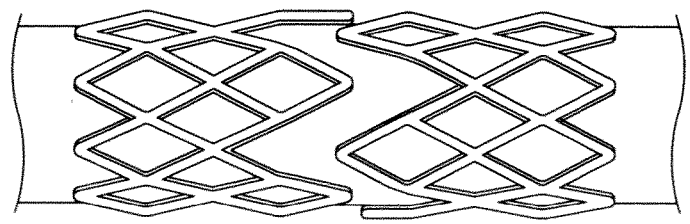

During balloon inflation, the diamond pattern will open up, for example, as shown in FIG. 30, which shows an exemplary deployment of a segmented scaffold. In FIG. 30, each segment shortens and opens independently of other segments. This is in contrast to deployment of segments 570 and 572 of FIG. 18A. During the initial stages of inflation the several heads at the ends of each segment will stay mechanically engaged behind the heads of the adjacent segment, thus holding the segment to segment relationship. As the segments are expanded further, the heads will move further apart circumferentially, as shown by arrows 599 in FIG. 18A, until they finally pass by each other with no more engagement near the fully deployed diameter. As a result, the natural longitudinal shortening of the diamonds in the segments and also the balloon lengthening which tends to increase the segment to segment gap during deployment have less of a contribution to the final segment to segment gap.

Therefore, the mechanical restraint during deployment provides several advantages. The segment to segment longitudinal relationship is maintained intact for a longer period of time, for example, for a longer period of time during deployment. This results in controlled and consistent final segment to segment gaps. In addition, the segment to segment circumferential relationship is maintained intact for a longer period of time. This results in less circumferential rotation of individual segments and thus a reduction in segment to segment collisions during vessel longitudinal compression. Reduction of collisions results in a reduced risk of vessel irritation, strut fracture, and emboli production.

Figure 19:
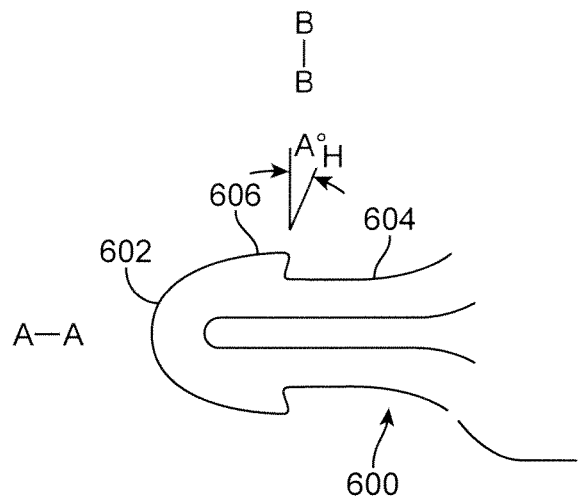
FIG. 19 depicts a portion of an end ring of a segment with a head portion and body portion.
Figure 20:
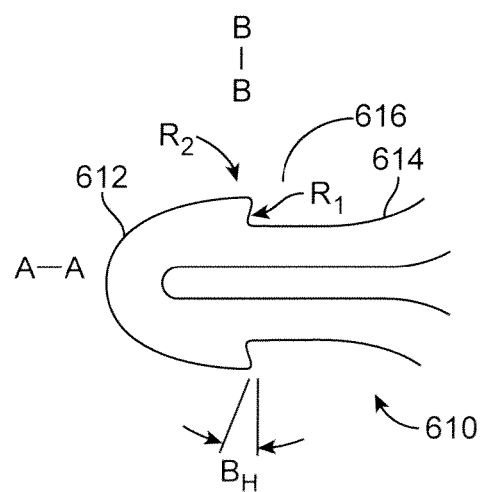
FIG. 20 depicts a portion of an end ring of a segment with a head portion and body portion.

FIGS. 19 and 20 depict alternative head designs. FIG. 19 depicts a portion 600 of an end ring of a segment with a head portion 602 and body portion 604. Line A-A is the longitudinal axis of the segment and line B-B is the circumferential direction. Overhangs 606 extend outward from body 604 with an angle $A_H$ with respect to line B-B, rotated toward the segment. This alternate head design enhances the longitudinal mechanical wedging interlocking effect of adjacent segments.

FIG. 20 depicts a portion 610 of an end ring of a segment with a head portion 612 and body portion 614. Line A-A is the longitudinal axis of the segment and line B-B is the circumferential direction. Overhangs 616 extend outward from body portion 614 with an angle $B_H$ with respect to line B-B, rotated away from the segment. The edges of the overhang at the head and body have radii of curvature $R_1$ and $R_2$, respectively. R1 will always be slightly less that R2 so that in the crimped state the R2 of one segment will have clearance at R1 to the struts of the adjacent segment. R2 may be 1%, 10%, 20%, 50%, 100% or greater than 100% of the height of one side of the head from strut 614. The alternate head design in FIG. 20 changes the mechanical characteristics of the head to head interaction. As $R_1$ and $R_2$ are varied, the diameter at which the interlocked heads separate is changed. This results in changes in segment spacing at final deployment.

The scaffold segments may be crimped tightly on a delivery balloon using a crimping apparatus such as an iris crimper. The crimping process may include two stages, a pre-crimping process and a final crimp process. In the pre-crimp process, the diameter of the scaffold segments are reduced to a diameter between the initial diameter and the balloon diameter prior to loading the scaffold segments on the balloon. The diameter of the segments can be reduced to the balloon diameter or 1 to 5% greater than the balloon diameter. For example, the pre-crimping process can crimp segments from a diameter of about 0.3 in to about 0.06 in.

The reason for the pre-crimp processes is to reduce the size of the scaffold segments to allow greater accuracy of loading the segments on the balloon with the desired degree of overlap or interlinking. A detailed discussion of a pre-crimping process for segmented scaffolds can be found in U.S. patent application Ser. No. 13/441,756.

In the pre-crimping process, the scaffold segments in an as-fabricated condition are placed over a mandrel and arranged end to end. The scaffold segments are spaced apart axially. The distance between the segments may be such that when the segments are reduced to the pre-crimp diameter the segments do not make contact with each other. For example, the scaffold segments are placed over a stepped mandrel. The mandrel with the scaffold segments is loaded into the pre-crimper, for example, an iris crimper and crimped to the pre-crimp diameter. The pre-crimped scaffold segments may further be placed inside a protective sheath disposed in an outer surface of the each scaffold segment.

The pre-crimped segments may then be loaded onto a balloon in a deflated state. The segments are placed over the balloon and arranged so that adjacent segments have a certain degree of overlap, for example, between 50 and 100%, or more narrowly, 50 to 60%, 60 to 70%, 70 to 80%, 80 to 90%, or 90 to 100%. The segments and balloon are then crimped down with pressure. The pressure may be applied at multiple steps with a dwell period between steps to achieve segment retention on the balloon. The balloon may be removed from the crimper one or more times, the removed segments pushed together to obtain a desired overlap and placed back into the crimper. Pressure may be applied to the balloon during the final stages of the crimp process to enhance the scaffold retention to the balloon in the crimped state. When the catheter is removed from the crimper a protective sheath may be placed over the scaffold segments.

Further embodiments of the present invention reduce or eliminate torsional or extension-compression forces on the rings of a scaffold and additionally address the sagging of vessel walls between scaffold segments. The embodiments can include scaffolds that are composed of segments that are not connected by linking elements or are connected by some linking elements.

In these embodiments, a scaffold having a plurality of segments in a crimped reduced configuration has at least one discontinuous linking element between adjacent segments. The scaffold can be crimped over a delivery balloon. The discontinuous linking elements extend from end of adjacent segments, however, do not connect the adjacent segments due to a discontinuity in the linking element located between the adjacent segments. Since the discontinuous linking elements do not connect the adjacent elements, the propagation of forces between the adjacent rings is reduced or eliminated. As a result, the scaffold is more fatigue and fracture resistant. Additionally, since the discontinuous link is structurally intact except for the discontinuity, the link can help support the lumen wall between segments once the scaffold is deployed in a vessel.

Figure 21:
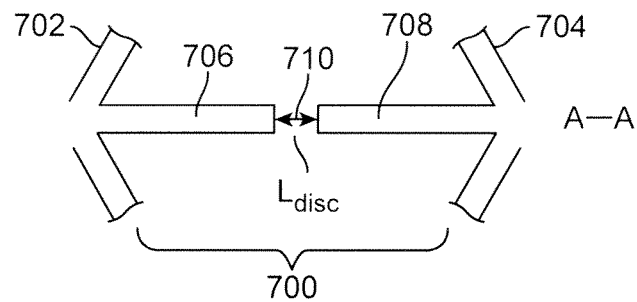
FIG. 21 depicts a close-up view of a discontinuous linking element between scaffold segments.

FIG. 21 depicts a close-up view of a discontinuous linking element 700 between scaffold segment 702 and scaffold segment 704. Discontinuous linking segment 700 includes a portion 706 connected to segment 702 and a portion 708 that is connected to segment 704. Linking strut 700 has a discontinuity, gap, or space 710 with a length $L_{disc}$ between the free ends of portion 706 and 708. $L_{disc}$ may be very small, for example, between 1 and microns. In general, the width may be 2 to 5, 5 to 10, 10 50 microns, or greater than 50 microns.

Figure 22:
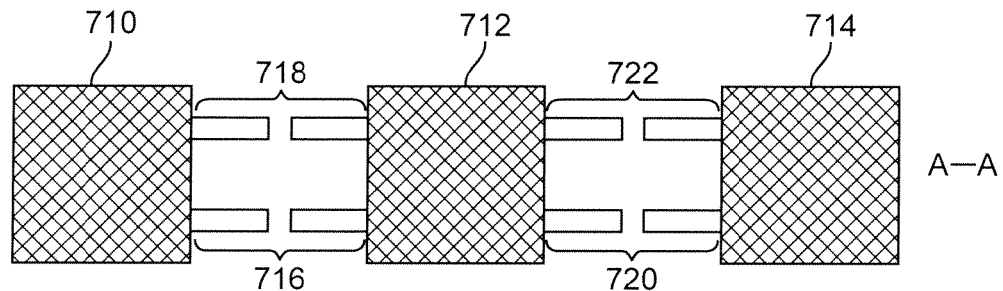
FIG. 22 depicts a two-dimensional projection of adjacent scaffold segments that are all disconnected.

In some embodiments, the scaffold has no linking elements between adjacent segments that connect adjacent segments with only discontinuous linking elements between segments so that all segments are disconnected. Adjacent segments may have 1, 2, 3, 4, 5 or more discontinuous linking elements between adjacent segments. FIG. 22 depicts a two-dimensional projection of adjacent scaffold segments that are disconnected. As shown in FIG. 22, scaffold segments 710, 712, and 714 are arranged end to end. Discontinuous linking elements 716 and 718 are between segments 710 and 712. Discontinuous linking elements 720 and 722 are between segments 712 and 714.

In other embodiments, the scaffold includes adjacent segments that are connected by at least one intact linking element. Therefore, adjacent scaffold segments are connected by at least one intact linking element and also include at least one discontinuous linking element.

Figure 23:
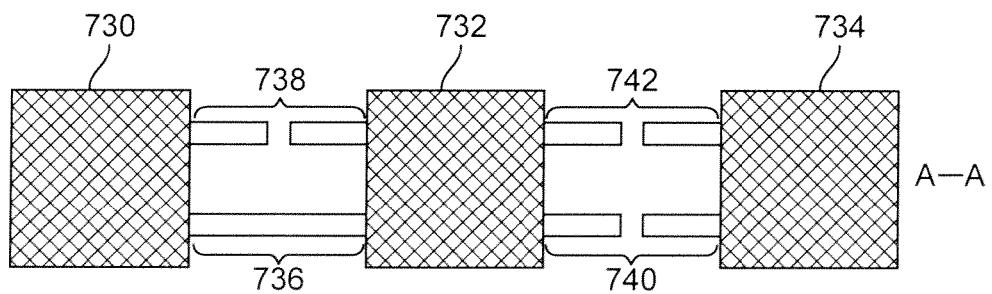
FIG. 23 depicts a two-dimensional projection of adjacent scaffold segments that include both intact and discontinuous linking elements.

FIG. 23 depicts a two-dimensional projection of adjacent scaffold segments that include both intact and discontinuous linking elements. As shown in FIG. 23, scaffold segments 730, 732, and 734 are arranged end to end. Scaffold segments 730 and 732 are connected by intact linking element 736 and scaffold segments 732 and 734 are connected by intact linking element 742. Discontinuous linking element 738 is between scaffold segments 730 and 732. Discontinuous linking element 740 is between scaffold segments 732 and 734.

In some embodiments, the intact linking elements can be frangible or designed to fail. Frangible linking elements have weakened portions that facilitate fracture or breaking of the linking element after the scaffold is deployed. Prior to fracture, the frangible linking element provides stability to the scaffold during crimping and for a time after deployment. However, at some time after deployment the frangible linking elements fracture or break at the weakened portion, disconnecting scaffold segments which then prevents transfer of forces between segments. Features that facilitate fracture include a narrowed portion of the linking element, such as notch, or holes through a linking element. Scaffolds disclosing frangible linking elements with various types of weakened portions are disclosed in US2011/0066225 and US2012/0065722.

The scaffold segments can have any structure or pattern. For example, the scaffold segments can have the structure of a plurality of rings composed of diamond-shaped elements formed of struts such as the exemplary scaffold segment depicted in FIG. 3A. Additionally, the segments can have a structure composed of cylindrical undulating or sinusoidal rings with alternating crests or peaks with the rings connected by linking elements, as depicted in FIG. 1.

Figure 24:
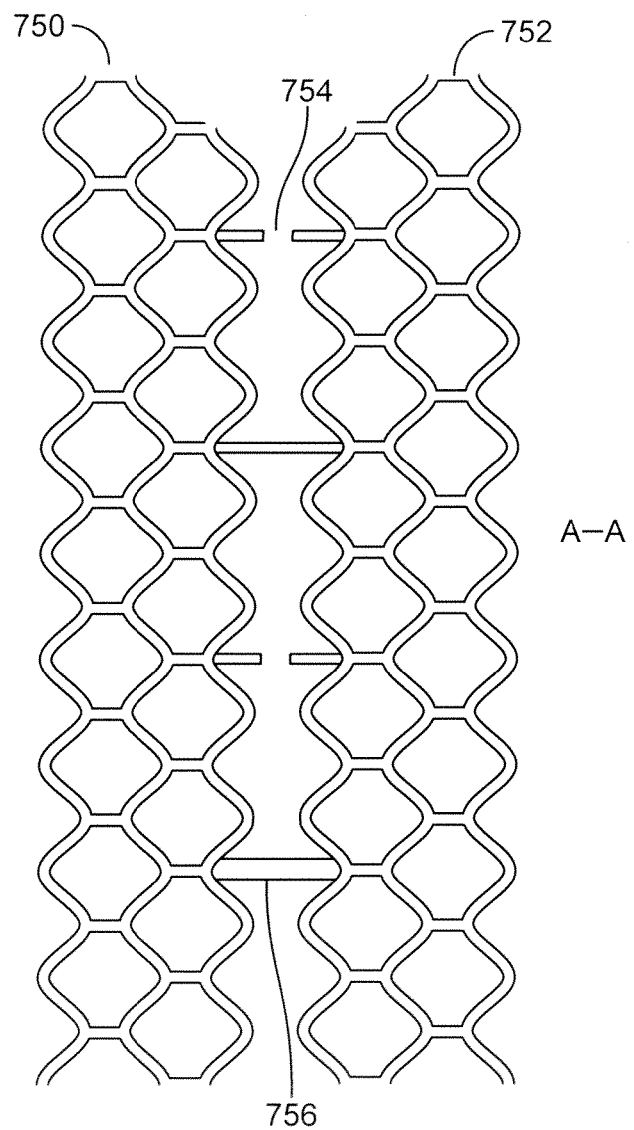
FIG. 24 depicts a close-up view of a region between scaffold segments, like those shown in FIG. 3A.

FIG. 24 depicts a close-up view of a region between segments 750 and 752, like those shown in FIG. 3A. The segments are shown in an expanded configuration rather than in a crimped configuration for ease of illustration. As shown, two discontinuous linking elements 754 and two intact linking segments 756 are disposed between segments 750 and 752. The number and arrangement of the intact and discontinuous linking elements is exemplary and any number and arrangement of linking elements between the ends of the segments is possible. In the example shown, one end of a linking element is connected to a trough of segment 750 and the other end is connected to a peak of segment 752. Alternatively, one end of a linking element can be connected to a peak of segment 750 and the other end may be connected to a trough of segment 752. In another alternative, segments 750 and 752 can be rotated relative to one another by one cell and one end of a linking element can be connected to the peak (or trough) of one segment and the other end of the linking element can be connected to the peak (or trough) of the other segment.

Figure 25:
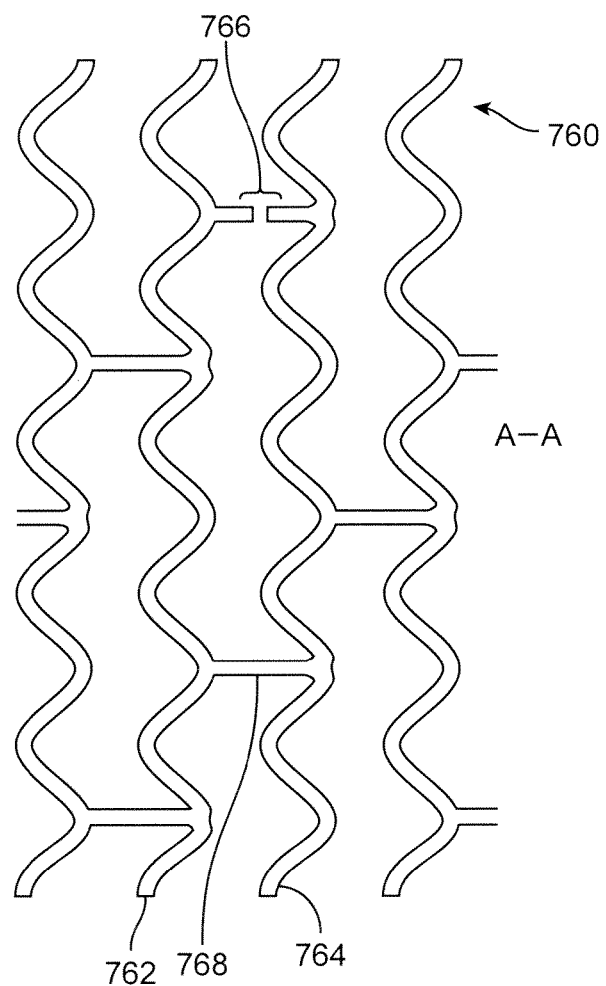
FIG. 25 depicts a close-up view of a portion of a scaffold like the one shown in FIG. 1.

FIG. 25 depicts a close-up view of a portion 760 of a scaffold like the one shown in FIG. 1. As shown in FIG. 25, two linking elements are between ring 762 and 764, a discontinuous linking element 766 and an intact linking element 768. Alternatively, both rings can be discontinuous linking elements so that the two rings are disconnected.

The scaffold of FIG. 1 is not designed specifically for use as a segmented scaffold, i.e., there are no pre-defined segments as in the segments of FIG. 3A. However, sets of rings can be identified as segments, where a set is one or more rings, e.g., rings 106 and 108 in FIG. 1. Discontinuous linking elements can be between every ring, every other ring, every third ring, etc., to form segments of one ring, two rings, three rings, etc. Segments can be connected by including at least one intact linking element. Segments can be disconnected by having no intact linking elements. Segments can be disconnected on both ends.

Figure 26:
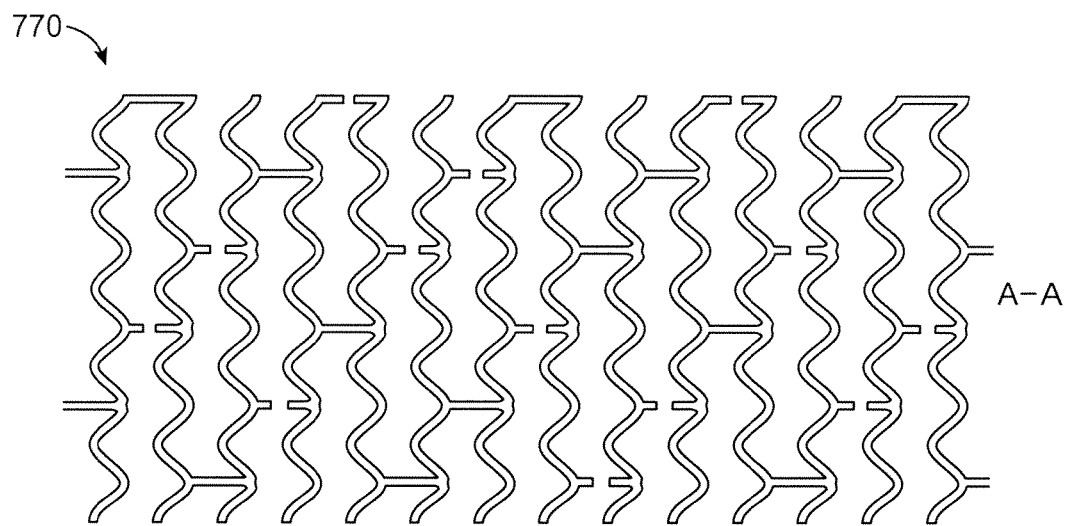
FIG. 26 depicts a pattern which is pattern from FIG. 1 with one discontinuous linking element and one intact linking element between each ring.
Figure 27:
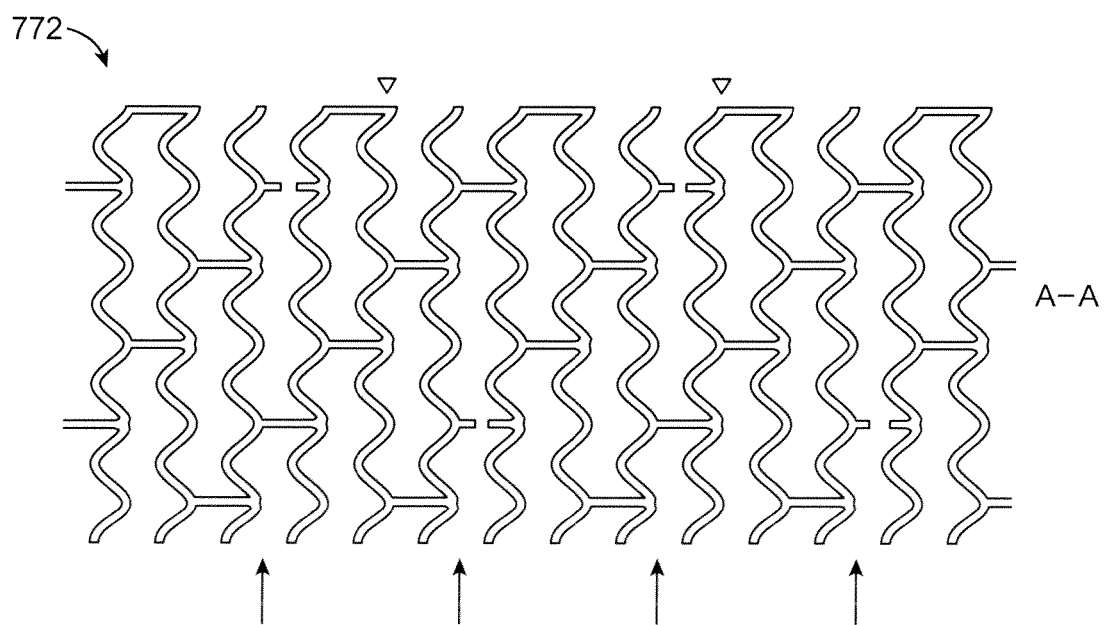
FIG. 27 depicts a pattern which is the pattern from FIG. 1 with one discontinuous linking element and one intact linking element at every third segment gap.

FIG. 26 depicts pattern 770 which is pattern 100 from FIG. 1 with one discontinuous linking element and one intact linking element between each ring. FIG. 27 depicts pattern 772 which is pattern 100 from FIG. 1 with one discontinuous linking element and one intact linking element at every third segment gap, as shown by the arrows. The segments consist of three rings.

Figure 28:
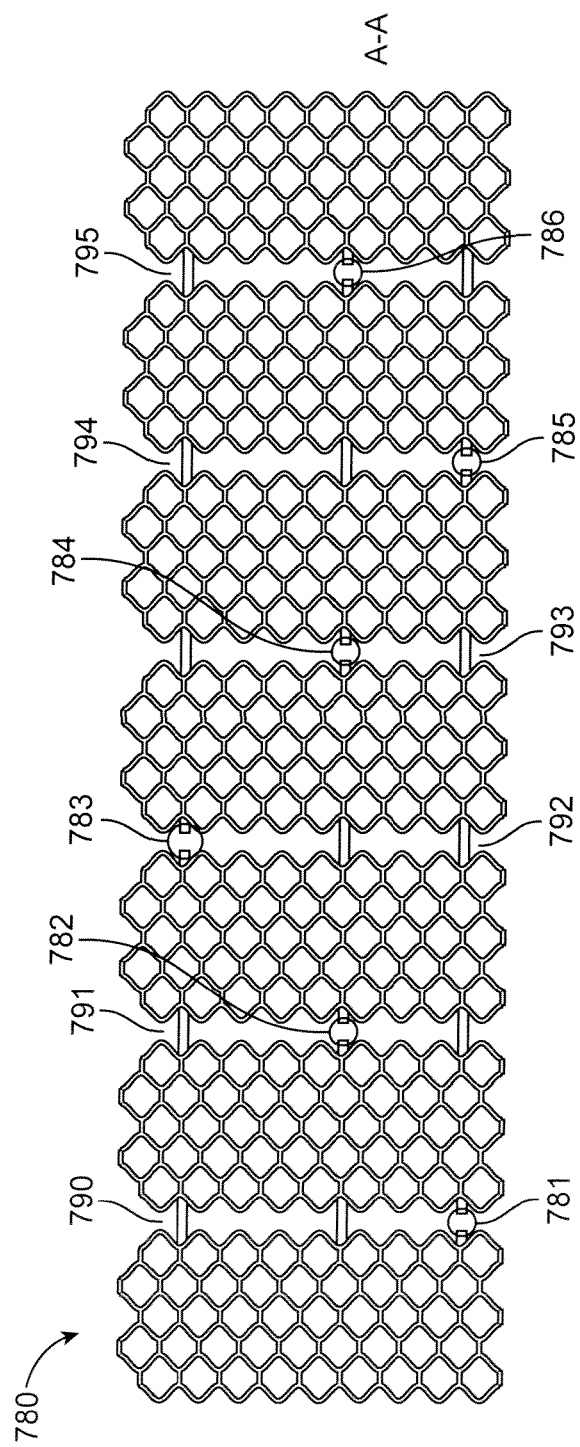
FIG. 28 depicts a segmented scaffold, which is the scaffold from FIG. 4 with two intact linking elements and two discontinuous linking elements between each segment.

In some embodiments, the disconnected linking elements may be arranged in a pattern along the length of the scaffold. Between the first end and second end of the scaffold, the disconnected linking elements may be offset circumferentially from one segment gap to the next. For example, the discontinuous linking elements can form a helical pattern. Offsetting the discontinuous linking elements tends to make the scaffold more stable once implanted. FIG. 28 depicts segmented scaffold 780, which is scaffold 340 from FIG. 4 with two intact linking elements and two discontinuous linking elements between each segment. Discontinuous linking elements 781-786 are offset circumferentially from gap to gap to form a helical pattern.

A scaffold with discontinuous linking elements can be formed from a scaffold with intact linking elements in a crimped reduced configuration. Scaffolds such as pattern or scaffold 100 in FIG. 1, pattern or scaffold 780 of FIG. 28 (with all linking elements intact) can be formed by laser machining a tube in an expanded configuration. The scaffold may then be crimped or pre-crimped to a reduced configuration. The discontinuous linking elements can be formed by laser cutting the selected linking elements.

The laser cutting can be performed with the scaffold crimped over a delivery balloon. Alternatively, the laser cutting can be performed with the scaffold crimped over a mandrel or some other support to prevent damage of the balloon by the laser. The scaffold may then be removed from the support and crimped over a delivery balloon. In another alternative, the scaffold may be crimped over delivery balloon with a protective sheath over the balloon to protect the balloon from the laser cutting. After laser cutting to create the discontinuous links, the protective sheath can be removed from the balloon by allowing a slight recoil in the scaffold and pulling off the sheath.

A further aspect of the present invention is variation of width of linking elements along the longitudinal axis. The variation in linking elements can include variation of width of intact linking elements and discontinuous linking elements. Certain sections of scaffold may be more susceptible to fracture from radial compression, torsion, flexion, and axial extension and compression. It is expected that the susceptibility to strut fracture depends on strut width. Therefore, the width of linking struts can account for the difference in the forces along the axis of the scaffold.

In these embodiments, the width of linking elements at segment gaps at the ends of a scaffold can be greater or less than the widths in a middle section. In an exemplary embodiment, the width of the linking elements at gaps at the two ends, gaps 790 and 791 and gaps 794 and 795 can be greater than the widths of the linking elements in gaps 792 and 793. The larger strut widths can be 10 to 100% larger, or more narrowly, 10 to 30%, 20 to 50%, or 40 to 80% larger.

The scaffold segments of the present invention can be made from variety of biodegradable polymers including, but not limited to, poly(L-lactide) (PLLA), polymandelide (PM), poly(DL-lactide) (PDLLA), polyglycolide (PGA), polycaprolactone (PCL), poly(trimethylene carbonate) (PTMC), polydioxanone (PDO), poly(4-hydroxy butyrate) (PHB), and poly(butylene succinate) (PBS). The scaffold segments can also be made from random and block copolymers of the above polymers, in particular, poly(L-lactide-co-glycolide) (PLGA) and poly(L-Lactide-co-caprolactone) PLGA-PCL. The scaffold can also be made of a physical blending of the above polymers. The scaffold segments can be made from PLGA including any molar ratio of L-lactide (LLA) to glycolide (GA). In particular, the stent can be made from PLGA with a molar ratio of (LA:GA) including 85:15 (or a range of 82:18 to 88:12), 95:5 (or a range of 93:7 to 97:3), or commercially available PLGA products identified as having these molar ratios. High strength, semicrystalline polymers with a Tg above body temperature include PLLA, PGA, and PLGA.

"Radial strength" is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely as only minimal additional force is required to cause major deformation. "Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

As used herein, the terms "axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e., radial strength.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to plastic deformation and then fracture. The ultimate strength is calculated from the maximum load applied during the test divided by the original cross-sectional area.

"Modulus" may be defined as the ratio of a component of stress or force per unit area applied to a material divided by the strain along an axis of applied force that result from the applied force. For example, a material has both a tensile and a compressive modulus.

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

EXAMPLES

Figure 29:
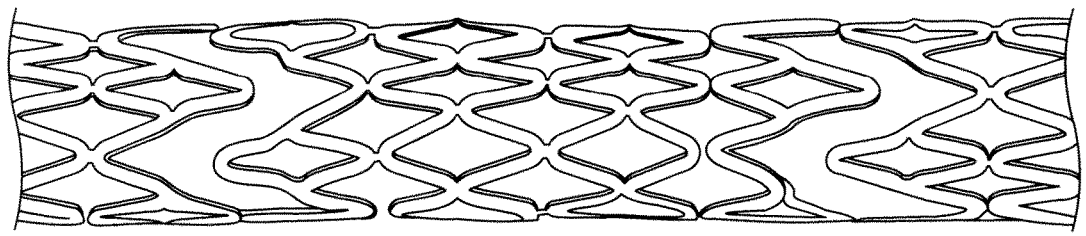
FIG. 29 is an image of interlinked segmented scaffold in a deployed state from a bench test.

FIG. 29 is an image of an interlinked segmented scaffold in a deployed state from a bench test. The middle segment is an off-set segment. As shown from the figure, there is no axial section all the way around the vessel wall that is not supported by a segment. Additionally, there is no sagging of the vessel wall inward the lumen in between the segments as is shown for the segmented scaffolds in FIG. 6. The vessel wall in FIG. 29 appears to be supported uniformly at the scaffold diameter along the entire length of the segmented scaffold.

FIG. 30 depicts images of an interlinked segmented scaffold composed of two segments. Diamonds are omitted only from one end of each segment. The uppermost image depicts the interlinked segments in a fully crimped state over a delivery balloon. The middle image depicts the interlinked segments in a semi-expanded state. The nonuniform or uneven expansion at the ends is due to the characteristic behavior of delivery balloons of inflating first at the ends. The degree of engagement of the segments increases from the crimped to the semi-expanded state. The uneven expansion causes sliding of the segments together which increases the engagement. The bottom image is the fully expanded scaffold showing the interlinking of the segments.

Figure 31:
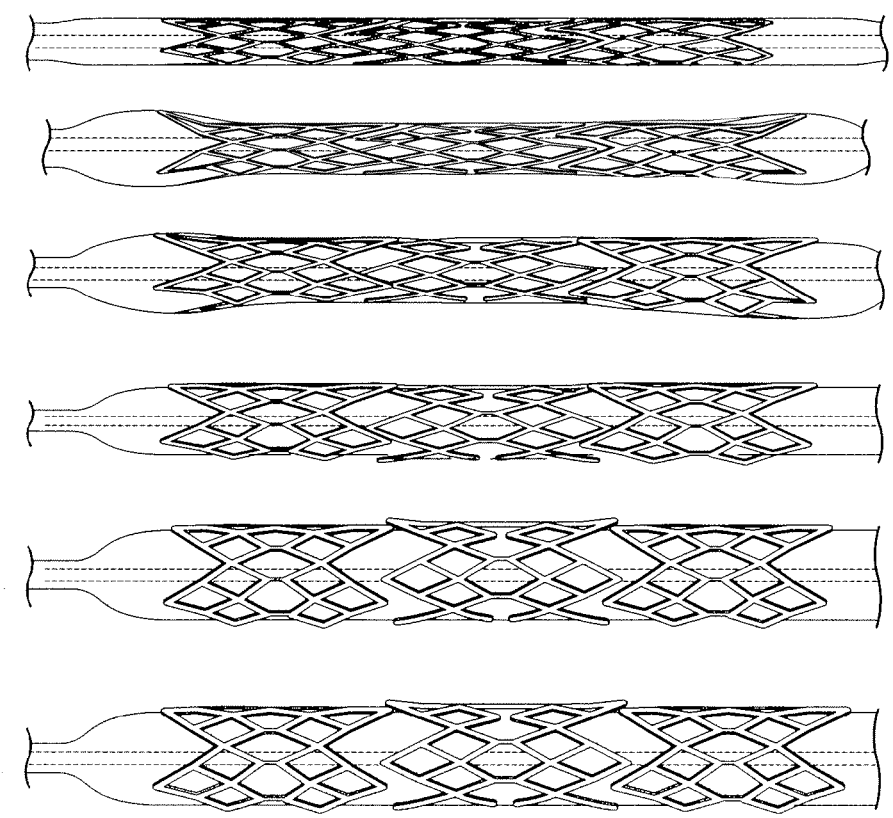
FIG. 31 depicts images of interlinked segmented scaffolds composed of three in-line segments.

FIG. 31 depicts images of interlinked segmented scaffolds composed of three in-line segments. The uppermost image depicts the three interlinked segments in a fully crimped state over a delivery balloon. The next two images depict the three interlinked segments undergoing uneven expansion. The next two images depict the three interlinked segments close to full expansion. The bottom image is the fully expanded scaffold showing the interlinking of the middle segment with the end segments. The end segments were observed not so slide on the balloon during the uneven expansion.

Figure 32:
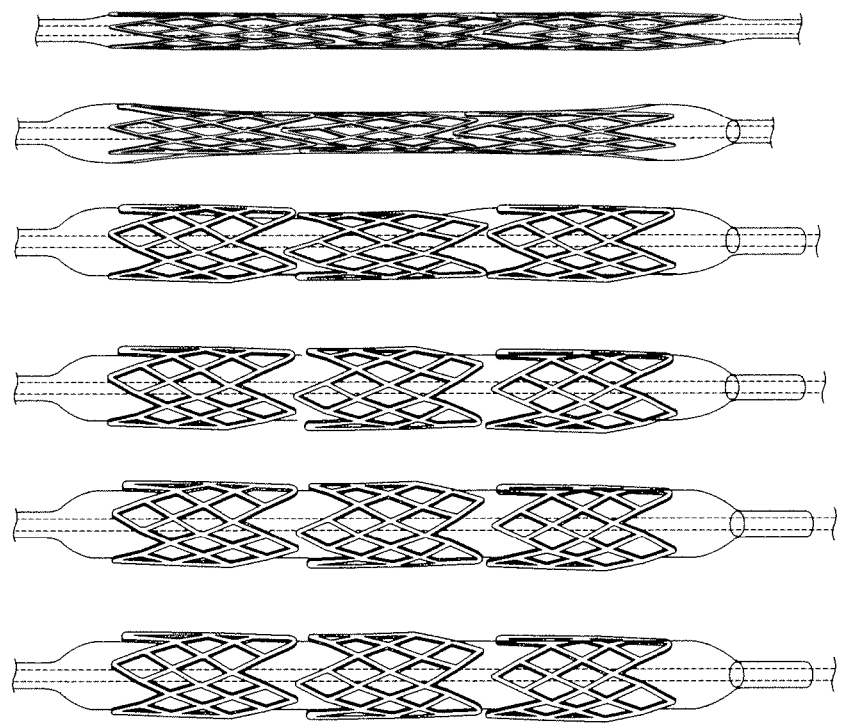
FIG. 32 depicts images of an interlinked segmented scaffold composed of three off-set segments.

FIG. 32 depicts images of an interlinked segmented scaffold composed of three off-set segments. The uppermost image depicts the three interlinked segments in a fully crimped state over a delivery balloon. The next two images depict the three interlinked segments undergoing uneven expansion. The next two images depict the three interlinked segments close to full expansion. The bottom image is the fully expanded scaffold showing interlinking of the middle segment with the end segments. The end segments were observed not so slide on the balloon during the uneven expansion. The segments end tips were in-line at full expansion.

Figure 33:
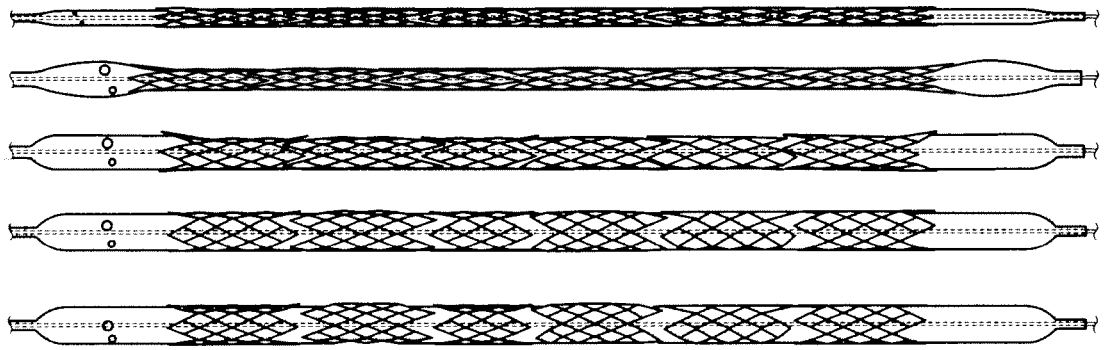
FIG. 33 depicts images of an interlinked scaffold segmented composed of six in-line segments.

FIG. 33 depicts images of an interlinked scaffold segmented composed of six in-line segments. The uppermost image depicts the five interlinked segments in a fully crimped state over a delivery balloon. The next two images depict the five interlinked segments undergoing uneven expansion. The fourth image depicts the five interlinked scaffolds close to full expansion. The bottom image is the fully expanded scaffold showing the interlinking adjacent segments. The segments were observed not so slide on the balloon during the uneven expansion.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A segmented scaffold, comprising:
   at least first and second radially expandable and disconnected polymer scaffold segments arranged end to end, each of the first and second segments comprising:
      undulating cylindrical rings composed of struts and forming a plurality of diamond-shaped cells, and
      a first ring at a first end and a second ring at a second end,
   wherein
      each of the first and second rings having alternating peak and valley undulations,
      a peak is formed by a side from three diamond-shaped cells,
      the peaks of the first ring extend in a first direction,
      the peaks of the second ring extend in a second direction opposite the first direction, and
      the peaks of the first ring are longitudinally aligned with the peaks of the second ring;

wherein
- the first ring of the second segment is arranged with the second ring of the first segment such that the peaks of the first ring of the second segment overlap the valleys of the second ring of the first segment;
- each segment being cut from a polymer tube or sheet,
- each segment configured for being crimped to a balloon, and
- prior to crimping each segment has a pre-crimp diameter and a length, and the length is at least 1.5 times the pre-crimp diameter.

2. The segmented scaffold of claim 1, wherein there are 2 to 6 or 2 to 3 undulating cylindrical rings per segment.

3. The segmented scaffold of claim 1, wherein a minimum length of the first segment is a longitudinal length of one diamond-shaped cell.

4. The segmented scaffold of claim 1, wherein the first segment has a maximum length equal to three-times a longitudinal length of a diamond-shaped cell.

* * * * *